United States Patent
Avital et al.

(10) Patent No.: US 11,170,508 B2
(45) Date of Patent: Nov. 9, 2021

(54) SYSTEMS AND METHODS FOR THE SEGMENTATION OF MULTI-MODAL IMAGE DATA

(71) Applicants: Ramot at Tel-Aviv University Ltd., Tel-Aviv (IL); Tel HaShomer Medical Research Infrastructure and Services Ltd., Ramat-Gan (IL)

(72) Inventors: Yitzhak Avital, Tel-Aviv (IL); Nahum Kiryati, Tel-Aviv (IL); Eli Konen, Ramat-Gan (IL); Arnaldo Mayer, Ramat-Gan (IL)

(73) Assignees: Ramot at Tel-Aviv University Ltd., Te;-Aviv (IL); Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 16/959,693

(22) PCT Filed: Jan. 3, 2019

(86) PCT No.: PCT/IL2019/050019
§ 371 (c)(1),
(2) Date: Jul. 2, 2020

(87) PCT Pub. No.: WO2019/135234
PCT Pub. Date: Jul. 11, 2019

(65) Prior Publication Data
US 2020/0380687 A1 Dec. 3, 2020

Related U.S. Application Data

(60) Provisional application No. 62/613,073, filed on Jan. 3, 2018.

(51) Int. Cl.
*G06T 7/11* (2017.01)
*G06N 3/08* (2006.01)
(Continued)

(52) U.S. Cl.
CPC .............. *G06T 7/11* (2017.01); *A61B 5/0042* (2013.01); *A61B 5/055* (2013.01); *A61B 5/4381* (2013.01);
(Continued)

(58) Field of Classification Search
CPC ........ G06K 7/1482; G06N 3/02; G06N 7/046; G06N 3/08; G06N 3/0454; G06N 3/082;
(Continued)

(56) References Cited

U.S. PATENT DOCUMENTS 10,499,857 B1 * 12/2019 Nguyen .................... G06N 3/08
2016/0093048 A1 * 3/2016 Cheng .................. G06K 9/6289
382/131

(Continued)

FOREIGN PATENT DOCUMENTS

WO WO 2017/106469 6/2017
WO WO 2019/135234 7/2019

OTHER PUBLICATIONS

Zhang, Wenlu, et al. "Deep convolutional neural networks for multi-modality isointense infant brain image segmentation." NeuroImage 108 (2015): 214-224. (Year: 2015).*

(Continued)

*Primary Examiner* — Siamak Harandi

(57) ABSTRACT

There is provided a computer implemented method of automatic segmentation of three dimensional (3D) anatomical region of interest(s) (ROI) that includes predefined anatomical structure(s) of a target individual, comprising: receiving 3D images of a target individual, each including the predefined anatomical structure(s), each 3D image is based on a different respective imaging modality. In one implementation, each respective 3D image is inputted into a respective processing component of a multi-modal neural network, wherein each processing component independently (Continued)

computes a respective intermediate, and the intermediate outputs are inputted into a common last convolutional layer(s) for computing the indication of segmented 3D ROI(s). In another implementation, each respective 3D image is inputted into a respective encoding-contracting component a multi-modal neural network, wherein each encoding-contracting component independently computes a respective intermediate output. The intermediate outputs are inputted into a single common decoding-expanding component for computing the indication of segmented 3D ROI(s).

19 Claims, 17 Drawing Sheets

(51) Int. Cl.
    *A61B 34/20*    (2016.01)
    *A61B 34/32*    (2016.01)
    *A61B 5/00*     (2006.01)
    *A61B 5/055*    (2006.01)
    *G01R 33/56*    (2006.01)

(52) U.S. Cl.
    CPC ............ *A61B 5/7267* (2013.01); *A61B 34/20* (2016.02); *A61B 34/32* (2016.02); *G01R 33/5602* (2013.01); *G01R 33/5608* (2013.01); *G06N 3/08* (2013.01); *G06T 2200/04* (2013.01); *G06T 2207/10092* (2013.01); *G06T 2207/20081* (2013.01); *G06T 2207/20084* (2013.01); *G06T 2207/20132* (2013.01); *G06T 2207/20156* (2013.01); *G06T 2207/30016* (2013.01); *G06T 2207/30081* (2013.01); *G06T 2207/30096* (2013.01)

(58) Field of Classification Search
    CPC ................... G06T 3/4046; G06T 9/002; G06T 2207/20084; G06T 7/11; G06T 2200/04; G06T 2207/10092; G06T 2207/20081; G06T 2207/20132; G06T 2207/20156; G06T 2207/30016; G06T 2207/30081; G06T 2207/30096; G06T 2207/10088; H03H 2017/0208; H03H 2222/04; G01R 33/5602; G01R 33/5608; A61B 34/20; A61B 34/32; A61B 5/0042; A61B 5/055; A61B 5/4381; A61B 5/7267; A61B 6/50; A61B 8/5207; A61B 6/501; A61B 6/032; A61B 6/037; A61B 6/466
    See application file for complete search history.

(56) References Cited

U.S. PATENT DOCUMENTS

| | | | | |
|---|---|---|---|---|
| 2017/0103532 | A1* | 4/2017 | Ghesu | A61B 8/0883 |
| 2017/0213339 | A1* | 7/2017 | Hibbard | A61B 6/5294 |
| 2018/0032846 | A1* | 2/2018 | Yang | G06K 9/4604 |
| 2018/0189572 | A1* | 7/2018 | Hori | G06F 16/783 |
| 2018/0374213 | A1* | 12/2018 | Arnold | A61B 5/0263 |
| 2019/0379605 | A1* | 12/2019 | Pfister | H04L 41/14 |

OTHER PUBLICATIONS

Nie, Dong, et al. "Fully convolutional networks for multi-modality isointense infant brain image segmentation." 2016 IEEE 13Th international symposium on biomedical imaging (ISBI). IEEE, 2016. (Year: 2016).*

Chen, Xiaozhi, et al. "Multi-view 3d object detection network for autonomous driving." Proceedings of the IEEE conference on Computer Vision and Pattern Recognition. 2017. (Year: 2017).*

Mehta, Raghav, and Jayanthi Sivaswamy. "M-net: A convolutional neural network for deep brain structure segmentation." 2017 IEEE 14th International Symposium on Biomedical Imaging (ISBI 2017). IEEE, 2017. (Year: 2017).*

International Search Report and the Written Opinion dated Apr. 15, 2019 From the International Searching Authority Re. Application No. PCT/IL2019/050019. (10 Pages).

Bick et al. "From Research to Clinical Practice: Implementation of Functional Magnetic Imaging and White Matter Tractography in the Clinical Environment", Journal of the Neurological Sciences, 312(1): 158-165, Available Online Aug. 23, 2011.

Chen et al. "Multi-View 3D Object Detection Network for Autonomous Driving", 2017 IEEE Conference on Computer Vision and Pattern Recognition, CVPR, Honolulu, HI, USA, Jul. 21-26, 2017, 1(2): 1907-1915, Jul. 21, 2017.

Cicek et al. "3D U-Net: Learning Dense Volumetric Segmentation From Sparse Annotation", Medical Image Computing and Computer-Assested Intervention, MICCAI 2016, LNCS 9901: 424-432, Published Online Oct. 2, 2016.

Dice "Measures of the Amount of Ecologic Association Between Species", Ecology, 26(3): 297-302, Jul. 1945.

Dolz et al. "3D Fully Convolutional Networks for Subcortical Segmentation in MRI: A Large-Scale Study", NeuroImage, 170: 456-470, Available Online Apr. 24, 2017.

Eitel et al. "Multimodal Deep Learning for Robust RGB-D Object Recognition", 2015 IEEE/RSJ International Conference on Intelligent Robots and Systems, IROS, Hamburg, Germany, Sep. 28-Oct. 2, 2015, p. 681-687, Sep. 28, 2015.

Fidon et al. "Generalised Wasserstein Dice Score for Imbalanced Multi-Class Segmentation Using Holistic Convolutional Networks", arXiv:1707.00478v4, p. 1-12, Aug. 29, 2017.

Goubran et al. "Automated Atlas-Based Seeding in Cortico-Spinal Tractography", Proceedings of the DTI Tractography for Neurosurgical Planning: A Grand Challenge, 14th International Conference on Medical Image Computing and Computer Assisted Intervention, MICCAI 2011, Toronto, Canada, Sep. 18, 2011, p. 25-29, Sep. 18, 2011.

Hamers et al. "Similarity Measures in Scientometric Research: The Jaccard Index Versus Salton's Cosine Formula", Information Processing & Management, 25(3): 315-318, May 1989.

He et al. "Delving Deep Into Rectifiers: Surpassing Human-Level Performance on ImageNet Classification", Proceedings of the 2015 IEEE International Conference on Computer Vision, ICCV '15, Santago de Chile, Chile, Dec. 7-13, 2015, p. 1026-1034, Dec. 7, 2015.

Kamnitsas et al. "Efficient Multi-Sclae 3D CNN With Fully Connected CRF for Accurate Brain Lesion Segmentation", Medical Image Analysis, 36: 61-78, Available Online Oct. 29, 2016.

Kingma et al. "ADAM: A Method for Stochastic Optimization", arXiv Preprint arXiv:1412.6980v7, p. 1-13, Jul. 20, 2015.

Ma et al. "Multimodal Convolutional Neural Networks for Matching Image and Sentence", arXiv Preprint arXiv: 1504.06063v5, p. 1-12, Aug. 29, 2015.

Milletari et al. "V-Net: Fully Convolutional Neural Network for Volumetric Medical Image Segmentation", Proceedings of the 2016 IEEE 4th International Conference on 3D Vision, 3DV, Stanford, CA, USA, Oct. 25-28, 2016, p. 565-571, Oct. 25, 2016.

Nie et al. "Fully Convolutional Networks for Multi-Modality Isointense Infant Brain Image Segmentation", Proceedings of the 2016 IEEE 13th International Symposium on Biomedical Imaging, ISBI, Prague, Czech Republic, Apr. 13-16, 2016, p. 1342-1345, Apr. 13, 2016.

O'Donnell et al. "Automated White Matter Fiber Tract Identification in Patients With Brain Tumors", NeuroImage: Clinical, 13: 138-153. Available Online Nov. 25, 2016.

Pajevic et al. "Color Schemes to Represent the Orientation of Anisotropic Tissues From Diffusion Tensor Data: Application to White Matter Fiber Tract Mapping in the Human Brain", Magnetic Resonance in Medicine, 42(3): 526-540, Sep. 1999.

Ronneberger et al. "U-Net: Convolutional Networks for Biomedical Image Segmentation", Proceedings of the International Conference on Medical Image Computing and Computer-Assisted Intervention, MICCAI 2015, LNCS, 9351: 234-241, Nov. 18, 2015.

(56) References Cited

OTHER PUBLICATIONS

Scherrer et al. "Automatic Delineation of White Matter Fascicles by Localization Based Upon Anatomical Spatial Relationships", Proceedings of the 2013 IEEE 10th International Symposium on Biomedical Imaging, ISBI, San Francisco, CA, USA, Apr. 7-11, 2013, p. 1146-1149, Apr. 7, 2013.

Sherbondy et al. "ConTrack: Finding the Most Likely Pathways Between Brain Regions Using Diffusion Tractography", Journal of Vision, 8(9): 1-16, Published Online Jul. 29, 2008.

Tunc et al. "Automated Tract Extraction Via Atlas Based Adaptive Clustering", NeuroImage, 102(Pt.2): 596-607, Nov. 15, 2014.

Zhang et al. "Deep Convolutional Neural Networks for Multi-Modality Isotense Infant Brain Image Segmentation", NeuroImage, 108: 214-224, Available Online Jan. 3, 2015.

\* cited by examiner

1302 →

| Tract | Box size [w,l,h] (mm) | Box ULPC offset from 3DBB (mm) |
|---|---|---|
| Arcuate | [128,90,112] | [0,10,0] |
| Motor | [128,90,112] | [0,50,0] |
| Optic rad. | [112,112,112] | [0,0,0] |

FIG. 13

|  | LGN | Calcarine | Brainstem | Precentral | Arcuate |
|---|---|---|---|---|---|
| Vnet-T1 | 0.6767 | 0.7377 | 0.6867 | 0.6880 | 0.5109 |
| Vnet-PDD | 0.6472 | 0.6993 | 0.8334 | 0.7085 | 0.5382 |
| Vnet-PDDT1 | 0.6493 | 0.6915 | 0.7947 | 0.7103 | 0.5384 |
| Wnet | 0.6458 | 0.7167 | 0.8099 | 0.6705 | 0.5243 |
| Ynet | 0.7031 | 0.7649 | 0.8454 | 0.713 | 0.5556 |

| | DICE | | | | |
|---|---|---|---|---|---|
| | Calcarine | LGN | Precentral | Brainstem | Arcuate |
| Vnet-T1 | 0.703 (0.14) | 0.687 (0.20) | 0.747 (0.14) | 0.664 (0.18) | 0.330 (0.32) |
| Vnet-PDD | 0.661 (0.13) | 0.732 (0.13) | 0.762 (0.10) | 0.806 (0.08) | 0.577 (0.26) |
| Vnet-PDDT1 | 0.696 (0.12) | 0.732 (0.13) | 0.768 (0.10) | 0.807 (0.07) | 0.348 (0.34) |
| Wnet | 0.662 (0.15) | 0.716 (0.16) | 0.721 (0.15) | 0.796 (0.01) | 0.588 (0.21) |
| Ynet | 0.718 (0.10) | 0.742 (0.13) | 0.775 (0.12) | 0.797 (0.11) | 0.602 (0.22) |

| Jaccard | | | | | |
|---|---|---|---|---|---|
| | Calcarine | LGN | Precentral | Brainstem | Arcuate |
| Vnet-T1 | 0.557 (0.14) | 0.551 (0.18) | 0.612 (0.15) | 0.520 (0.17) | 0.246 (0.26) |
| Vnet-PDD | 0.506 (0.13) | 0.592 (0.15) | 0.622 (0.10) | 0.682 (0.10) | 0.435 (0.20) |
| Vnet-PDDT1 | 0.544 (0.12) | 0.591 (0.14) | 0.633 (0.12) | 0.683 (0.10) | 0.266 (0.27) |
| Wnet | 0.511 (0.15) | 0.578 (0.17) | 0.582 (0.15) | 0.671 (0.12) | 0.445 (0.20) |
| Ynet | 0.568 (0.11) | 0.603 (0.14) | 0.646 (0.13) | 0.673 (0.12) | 0.461 (0.20) |

| | Optic Radiation | Motor tracts |
|---|---|---|
| Number of reconstructed fibers | 30.000 | 30.000 |
| Min. fiber length (mm) | 35 | 55 |
| Max. fiber length (mm) | 150 | 185 |
| Number of best fibers kept (K) | 15.000 | 25.000 |

| | |
|---|---|
| Step size (mm) | 1 |
| Angle threshold (deg.) | 75 |
| FA threshold | 0.1 |
| Min tract length (mm) | 35 |
| Interpolation | linear |

| DICE - fibers tracts | | | |
|---|---|---|---|
| | Optic rad. | Motor | Arcuate |
| Vnet-T1 | 0.596 (0.13) | 0.660 (0.10) | 0.648 (0.16) |
| Vnet-PDD | 0.615 (0.09) | 0.706 (0.07) | 0.679 (0.17) |
| Vnet PDDT1 | 0.629 (0.07) | 0.676 (0.07) | 0.679 (0.17) |
| Wnet | 0.589 (0.12) | 0.656 (0.10) | 0.674 (0.16) |
| Ynet | 0.633 (0.07) | 0.679 (0.09) | 0.698 (0.17) |

SYSTEMS AND METHODS FOR THE SEGMENTATION OF MULTI-MODAL IMAGE DATA

RELATED APPLICATIONS

This application is a National Phase of PCT Patent Application No. PCT/IL2019/050019 having International filing date of Jan. 3, 2019, which claims the benefit of priority under 35 USC § 119(e) of U.S. Provisional Patent Application No. 62/613,073 filed on Jan. 3, 2018. The contents of the above applications are all incorporated by reference as if fully set forth herein in their entirety.

BACKGROUND

The present invention, in some embodiments thereof, relates to neural networks for image processing and, more specifically, but not exclusively, to systems and methods for automated segmentation of multi-modal images.

Segmentation of anatomical structures finds application in different fields of medicine. For example, in the field of neuro-surgical navigation, anatomical ROIs, which in practice are manually segmented by a neuro-anatomy expert on a three dimensional (3D) image of the brain, act as seed points for computation of white matter tractography. Tractography is an important mapping tool for neuro-surgical planning and navigation, which is limited by stringent pre-op time-constraints and limited availability of neuro-anatomy experts for manual segmentation of the seed ROIs. In another example, segmentation of the prostate may be used for computing the prostate volume, map the different tissues of the prostate, including tumors and, accordingly, planning procedures or treatments on the prostate.

SUMMARY

According to a first aspect, a computer implemented method of automatic segmentation of at least one three dimensional (3D) anatomical region of interest (ROI) that includes at least one predefined anatomical structure of a target individual, comprises: receiving a plurality of 3D images of a target individual, each 3D image of the plurality of 3D images including the at least one predefined anatomical structure, each 3D image of the plurality of 3D images is based on a different respective imaging modality, inputting each respective 3D image of the plurality of 3D images into a respective processing component of a plurality of processing components of a multi-modal neural network, wherein each processing component of the multi-modal neural network independently computes a respective intermediate output of a plurality of intermediate outputs for the corresponding respective 3D image of the plurality of 3D images, inputting the plurality of intermediate outputs into a common at least one last convolutional layer, and computing an indication of a segmented at least one 3D ROI that includes the at least one predefined anatomical structure, for each of the plurality of 3D images, by the common at least one last convolutional layer.

According to a second aspect, a system for automatic segmentation of at least one three dimensional (3D) anatomical region of interest (ROI) that includes at least one predefined anatomical structure of a target individual, comprises: at least one hardware processor executing a code for: receiving a plurality of 3D images of a target individual, each 3D image of the plurality of 3D images including the at least one predefined anatomical structure, each 3D image of the plurality of 3D images is based on a different respective imaging modality, inputting each respective 3D image of the plurality of 3D images into a respective processing component of a plurality of processing components of a multi-modal neural network, wherein each processing component of the multi-modal neural network independently computes a respective intermediate output of a plurality of intermediate outputs for the corresponding respective 3D image of the plurality of 3D images, inputting the plurality of intermediate outputs into a common at least one last convolutional layer, and computing an indication of a segmented at least one 3D ROI that includes the at least one predefined anatomical structure, for each of the plurality of 3D images, by the common at least one last convolutional layer.

According to a third aspect, a computer implemented method of automatic segmentation of at least one three dimensional (3D) anatomical region of interest (ROI) that includes at least one predefined anatomical structure of a target individual, comprises: receiving a plurality of 3D images of a target individual, each 3D image of the plurality of 3D images including the at least one predefined anatomical structure, each 3D image of the plurality of 3D images is based on a different respective imaging modality, inputting each respective 3D image of the plurality of 3D images into a respective encoding-contracting component of a plurality of encoding-contracting components of a multi-modal neural network, wherein each encoding-contracting component of the multi-modal neural network independently computes a respective intermediate output of a plurality of intermediate outputs for the corresponding respective 3D image of the plurality of 3D images, inputting the plurality of intermediate outputs into a single common decoding-expanding component of the multi-modal neural network, and computing an indication of a segmented at least one 3D ROI that includes the at least one predefined anatomical structure for each of the plurality of 3D images by the single common decoding-expanding component, wherein each stage of the single common decoding-expansion path is concatenated by skips of a plurality of outputs generated by each corresponding stage of each of the plurality of encoding-contracting components.

According to a fourth aspect, a system for automatic segmentation of at least one three dimensional (3D) anatomical region of interest (ROI) that includes at least one predefined anatomical structure of a target individual, comprises: at least one hardware processor executing a code for: receiving a plurality of 3D images of a target individual, each 3D image of the plurality of 3D images including the at least one predefined anatomical structure, each 3D image of the plurality of 3D images is based on a different respective imaging modality, inputting each respective 3D image of the plurality of 3D images into a respective encoding-contracting component of a plurality of encoding-contracting components of a multi-modal neural network, wherein each encoding-contracting component of the multi-modal neural network independently computes a respective intermediate output of a plurality of intermediate outputs for the corresponding respective 3D image of the plurality of 3D images, inputting the plurality of intermediate outputs into a single common decoding-expanding component of the multi-modal neural network, and computing an indication of a segmented at least one 3D ROI that includes the at least one predefined anatomical structure for each of the plurality of 3D images by the single common decoding-expanding component, wherein each stage of the single common decoding-expansion path is concatenated by skips of a plurality of outputs generated by each corresponding stage of each of the plurality of encoding-contracting components.

According to a fifth aspect, a computer implemented method of training a multi-modal neural network for outputting an automatic segmentation of at least one three dimensional (3D) anatomical region of interest (ROI) that includes at least one predefined anatomical structure of a target individual, comprises: receiving a plurality of training sets each of a respective sample individual, each training set including a plurality of registered 3D images created based on different imaging modalities and depicting at least one predefined anatomical structure, receiving, for each of the plurality of training sets, a 3D segmentation of at least one anatomical ROI that includes the at least one predefined anatomical structure for each of the plurality of registered 3D images of the respective training sets, and training a multi-modal neural network to compute the at least one anatomical ROI that includes the at least one predefined anatomical structure according to an input of a set of a plurality of registered 3D images based on the different imaging modalities, wherein each processing component of the multi-modal neural network independently computes a respective intermediate output of a plurality of intermediate outputs for the corresponding respective 3D image of the plurality of 3D images, wherein the plurality of intermediate outputs of the plurality of processing components are merged before at least one last convolutional layer of the multi-modal neural network and the merged plurality of intermediate outputs are inputted into the at least one last convolutional layer.

According to a sixth aspect, a computer implemented method of training a multi-modal neural network for outputting an automatic segmentation of at least one three dimensional (3D) anatomical region of interest (ROI) that includes at least one predefined anatomical structure of a target individual, comprises: receiving a plurality of training sets each of a respective sample individual, each training set including a plurality of registered 3D images created based on different imaging modalities and depicting at least one predefined anatomical structure, receiving, for each of the plurality of training sets, a 3D segmentation of at least one anatomical ROI that includes the at least one predefined anatomical structure for each of the plurality of registered 3D images of the respective training sets, and training a multi-modal neural network to compute the at least one anatomical ROI that includes the at least one predefined anatomical structure according to an input of a set of a plurality of registered 3D images based on the different imaging modalities, wherein each encoding-contracting component of a plurality of encoding-contracting components of the multi-modal neural network independently computes a respective intermediate output of a plurality of intermediate outputs for the corresponding respective 3D image of the plurality of 3D images, wherein the plurality of intermediate outputs are inputted into a single common decoding-expanding component of the multi-modal neural network, wherein each step of the single common decoding-expansion component is concatenated by skips of the plurality of outputs generated for each corresponding step of each of the plurality of encoding-contracting components.

The systems and/or apparatus and/or methods and/or code instructions (e.g., stored in a data storage device executable by one or more hardware processors) described herein provide a technical solution to the technical problem of automatically segmenting one or more 3D anatomical ROIs from a 3D anatomical image of a target individual. The 3D anatomical ROIs may be provided, for example, as input into code instructions that automatically compute one or more 3D white matter tracts of the brain (referred to as tractography"), for example, for in-vivo, pre-operative, and/or intra-operative mapping of connectivity of the brain of the target individual. In another example, the 3D anatomical ROIs may be provided as input into code instructions that automatically computes the prostate volume, map the different tissues of the prostate, including tumors and, accordingly, planning procedures and/or treatments on the prostate.

3D segmentation of anatomical ROIs is technically challenging, since the 3D anatomical ROIs, which have complex shapes, may appear differently in different people, for example, due to deformations and/or variations resulting from tumors, genetic anatomical variability, other abnormalities, and/or imaging artifacts.

The systems and/or apparatus and/or methods and/or code instructions described herein improve the technical field of automated 3D segmentation of 3D anatomical images, in comparison to other known automated 3D segmentation processes. The improvement may be provided, for example, in terms of accuracy of the 3D segmentation. The improvement may arise due to the multi-modal architecture of the classifier(s) described herein, that perform segmentation based on two or more anatomical imaging data acquired by two or more anatomical imaging modalities, optionally 3D imaging modalities. The improvement may arise due to the architectures of the multi-modal classifiers described herein, that include different implementations for integrating data from the two or more images acquired by the two or more imaging modalities.

The systems and/or apparatus and/or methods and/or code instructions described herein provide a technical advantage of a computational device that automatically computes the 3D anatomical ROIs and/or of the computational device that performs tractography mapping according to the 3D anatomical ROIs, by reducing the ROI delineation time to almost zero in particular in comparison to manual delineation of the ROIs which may take for example 1-3 hours, and/or provides fully automated tractography mapping without necessarily requiring human intervention and/or reducing human intervention.

The systems, apparatus, methods and/or code instructions (stored in a data storage device, executable by one or more hardware processors) described herein are directed to an improvement in computer-related technology, by improving the ability of computers to automatically segment predefined anatomical regions based on multi-modal images. Such 3D segmentation could only be properly performed by a human expert trained in the relevant medical field. Such manual segmentation is based on for example, instinct and/or experience. Other computer automated methods perform segmentation for a single 3D image, which results in a less accurate segmentation that performing multi-modal segmentation as described herein. Yet other computer automated methods perform segmentation independently for different 3D image, which results in a less accurate segmentation that performing multi-modal segmentation as described herein. However, it is noted that the systems, apparatus, methods and/or code instructions described herein are not merely a computer-implemented version of a mental process or intended to simply replicate or model human capability, but provide an improvement in the ability to segment complex anatomical structures which vary in location and/or geometric between individuals. The systems, apparatus, methods and/or code instructions described herein generate a new user experience, based on a new workflow pattern.

At least some systems, methods, apparatus, and/or code instructions described herein improve the medical and/or technological field of automated 3D segmentation of anatomical structures in 3D images, optionally complex anatomical structures such as in the brain. Using standard methods, a user (e.g., neuroradiologist, neurologist, neurosurgeon) manually examines the 3D images and manually performs the 3D segmentation. Such manual analysis is subjective, based on the individual user performing the segmentation, leading to inaccuracies which may arise from subjective experiences of the user performing the segmentation. Moreover, segmentation is technically challenging due to inter-subject variability, in which corresponding anatomical structures appears differently in different patients. Inter-subject variability may arise, for example, due to deformations of the anatomy, for example, due to tumors. The deformation may result in the target anatomical region being located at a different place than normally expected (e.g., shifted) and/or having a different shape than normally expected (e.g., due to deformation of its original shape by the tumor).

In a further implementation form of the first and second aspects, each of the plurality of processing components includes an encoding-contracting path for capturing context based on a plurality of computed feature channels, and a decoding-expanding path for localization based on the computed features.

In a further implementation form of the first and second aspects, the at least one last convolutional layer comprises a fully connected layer.

In a further implementation form of the first and second aspects, features extracted from stages of the encoding-decoding path are forwarded to corresponding stages of the decoding-expanding path for gathering fine grained detail that would otherwise be lost in compression computations of the encoding-contracting path.

In a further implementation form of the first, second, third, and fourth aspects, the plurality of 3D images are registered to one another, and wherein the indication of the segmentation of the at least one 3D ROI is associated with each of the plurality of registered 3D image.

In a further implementation form of the first, second, third, and fourth aspects, the plurality of 3D images include a 3D MRI anatomical image of a brain of a target individual, and a 3D diffusion tensor imaging (DTI) image of the brain indicative of principal direction of diffusion (PDD), and the at least one 3D ROI includes at least one predefined brain structure.

In a further implementation form of the first, second, third, and fourth aspects, the 3D anatomical image comprises a T1w magnetic resonance imaging (MRI) image of the brain containing data insufficient for imaging of at least one white matter tract, and the 3D DTI image indicative of PDD comprises a color map.

In a further implementation form of the first, second, third, and fourth aspects, the indication of the segmented at least one 3D ROI is of a brain of a target individual, the indication is provided as a substitute for a region identified based on a functional MRI (fMRI) mapping based on cooperation by the target individual, for input into a brain surgery planning process.

In a further implementation form of the first, second, third, and fourth aspects, the method and/or system further comprise computing at least one 3D white matter tract of the brain of the target individual by designating a segmented at least one 3D anatomical ROI as a seed of the DTI image of the brain.

In a further implementation form of the first, second, third, and fourth aspects, the plurality of 3D images include a T2 weighted MRI scan that includes a prostate, a diffusion weighted MRI that includes the prostate, and a dynamic contrast enhanced scan of the prostate, wherein the at least one 3D ROI includes the prostate.

In a further implementation form of the first, second, third, and fourth aspects, the multi-modal neural network comprises a 3D multi-modal fully convolutional neural network (FCNN).

In a further implementation form of the first, second, third, and fourth aspects, a plurality of 3D anatomical ROIs are segmented in parallel.

In a further implementation form of the first and second aspects, a number of 3D voxel filters at each stage of a plurality of stages of the instances of the common component of the multi-modal neural network respectively comprise 10, 20, 40, 80, and 160.

In a further implementation form of the first and second aspects, each processing component of the plurality of processing components includes a plurality of 3D filters, concatenation skips between parallel stages, residual skips in each stage, convolutions and deconvolutions for down and up-sampling, followed by dropout layers.

In a further implementation form of the first, second, third, and fourth aspects, the method and/or system further comprise generating instructions according to the segmented at least one 3D ROI for execution by at least one hardware processor.

In a further implementation form of the first, second, third, and fourth aspects, the instructions are selected from the group consisting of: automatically computing tractography using the at least one 3D ROI, automated surgery by a surgical robot for operating on the at least one 3D ROI, surgical planning for surgery on the at least one 3D ROI, and surgical assistance during surgery on the at least one 3D ROI.

In a further implementation form of the first, second, third, and fourth aspects, the segmented at least one 3D ROI are selected from the group consisting of: lateral geniculate nucleus (LGN) of the thalamus, calcarine sulcus in the occipital lobe, precentral-gyrus (posterior frontal lobe), brain stem, Wernicke area, and Broca area, motor tract, sensory tract, arcuate fasciculus, optic radiation tract, and prostate tissues including tumors and lesions.

In a further implementation form of the first, second, third, and fourth aspects, the method and/or system further comprise automatically computing brain tracts by at least one processor that executes code for automated tractography using the at least one 3D ROI as a seed ROI, selected from the group consisting of: computing an optic radiation tract using the LGN and calcarine sulcus segmented ROIs as seed ROIs, computing a motor tract using the precentral-gyrus and brain stem segmented ROIs as seed ROIs, and computing an arcuate tract using the Wernicke and Broca segmented ROIs as seed ROIs.

In a further implementation form of the first, second, third, and fourth aspects, the segmented at least one 3D ROI is a brain structure including at least one of: at least one white matter tract, at least one gray matter structure, and a combination of the aforementioned.

In a further implementation form of the third and fourth aspects, each encoding-contracting component captures context based on a plurality of feature channels computed by each stage for the respective 3D image.

In a further implementation form of the third and fourth aspects, the common decoding-expanding component performs localization based on the computed features.

In a further implementation form of the fifth and sixth aspects, the multi-modal neural network is trained according to maximization of an objective function based on the registered 3D images indicative of an imbalance between the number of voxels associated with a plurality of 3D anatomical ROIs segmented in parallel and background denoted by the voxels associated with the remaining tissue external to the anatomical ROIs.

In a further implementation form of the fifth and sixth aspects, the objective function denoted as MeanDice is computed according to the relationship:

$$MeanDice = \frac{1}{L}\sum_{l=1}^{L} D_l$$

wherein:

$$D_l = \frac{2\sum_{i}^{N} p_{li}g_{li}}{\sum_{i}^{N} p_{li}^2 + \sum_{i}^{N} g_{li}^2},$$

$p_{li} \in [0,1]$ denotes a softmax score computed for label l in voxel i, $g_{li}$ denotes a binary value indicative of ground truth label l in voxel i.

In a further implementation form of the fifth and sixth aspects, the method further comprises cropping each of the plurality of registered 3D images to predefined voxel dimensions defined by a cuboid bounding box including the 3D segmentation of at least one anatomical ROI.

In a further implementation form of the fifth and sixth aspects, the cuboid bounding box is computed according to a reference cuboid bounding box automatically extracted from a reference image of the respective sample individual that includes the at least one predefined anatomical structure.

In a further implementation form of the fifth and sixth aspects, each 3D image of the plurality of 3D images is rigidly registered with the other corresponding 3D images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 13 is a table summarizing a fixed size cropping box that is defined and positioned for each tract type, for the computational evaluation, in accordance with some embodiments of the present invention;

FIG. 16 is a table summarizing AUC for the evaluated classifiers of the computational evaluation, in accordance with some embodiments of the present invention;

FIG. 17 which is a table summarizing mean (standard deviation) of the Dice coefficient for sROIs segmentation over the 5 cross-validation folds of the computational evaluation, in accordance with some embodiments of the present invention;

FIG. 18 is a table summarizing mean (standard deviation) of the Jaccard coefficient for SROIs segmentation over all the 5 cross-validation folds of the computational evaluation, in accordance with some embodiments of the present invention;

FIG. 19 is a table presenting main parameter values for probabilistic tractography of the optic radiation and motor tracts of the computational evaluation, in accordance with some embodiments of the present invention;

FIG. 20 is a table presenting main parameter values for the deterministic tractography of the Arcuate tracts of the computational evaluation, in accordance with some embodiments of the present invention;

FIG. 21 is a table presenting mean (and standard deviation) of the Dice overlap coefficient of the fiber tracts computing by tractography for the computational evaluation, in accordance with some embodiments of the present invention.

DETAILED DESCRIPTION

Figure 1:
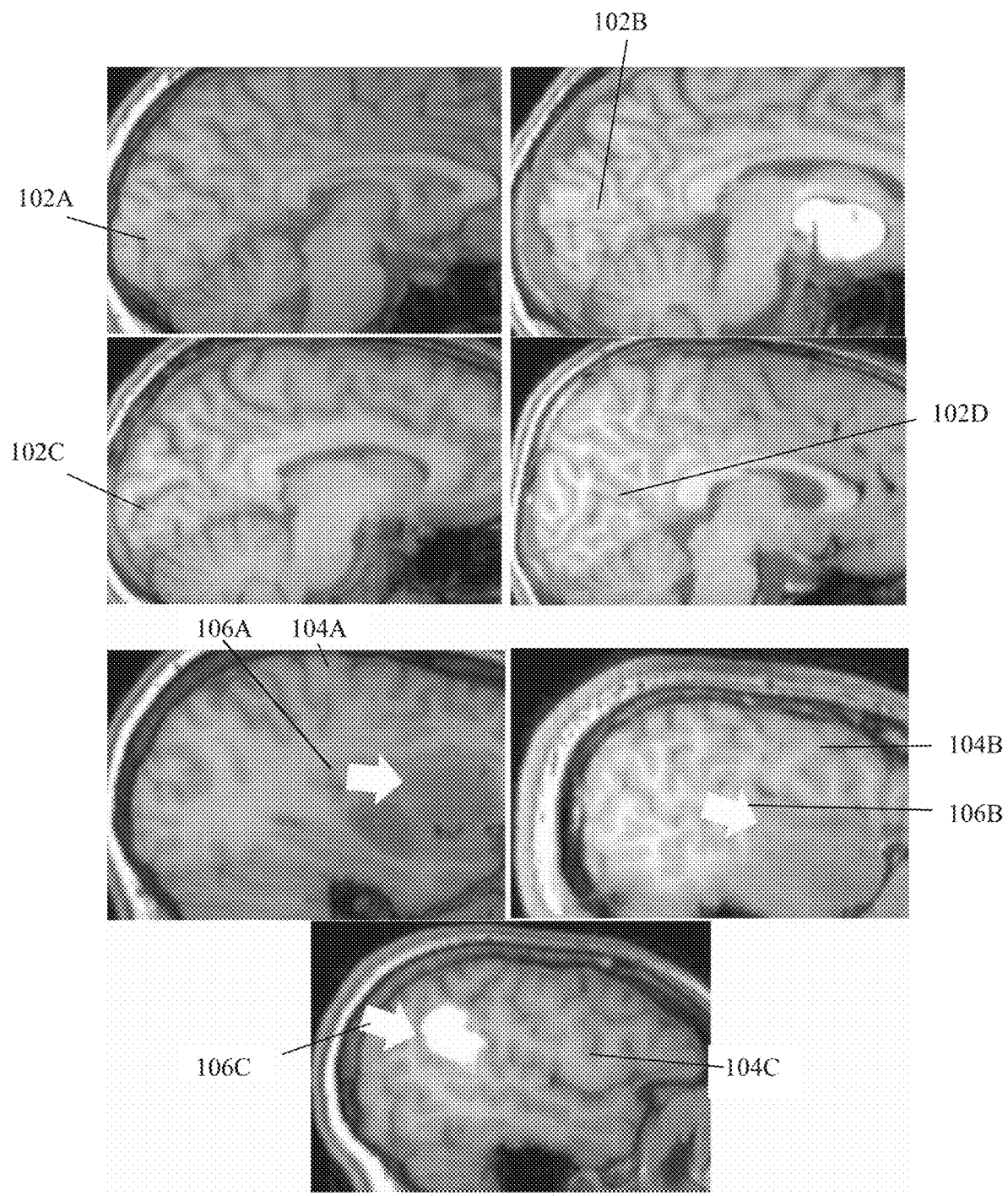
FIG. 1 includes images of different brains depicting the problem of inter-subject variability, to help understand technological improvements provided by some embodiments of the present invention.

The present invention, in some embodiments thereof, relates to neural networks for image processing and, more specifically, but not exclusively, to systems and methods for automated segmentation of multi-modal images.

As used herein, the term multi-modal images refers to a set of images, each based on a different imaging modality and/or based on a common imaging device with different image processing approaches. For example, anatomical (e.g., MRI T1w) images and white matter orientation pattern images (e.g., color DTI maps). In another example, CT images obtained with contrast, and CT images obtained without contrast. In another example, MRI images and CT images. The term multi-modal refers to two or more imaging modalities.

Each image of the multi-modal images may be processed as a respective image channel.

As used herein, the term region of interest (ROI) and seeding ROI (sROI) may sometimes be interchanged. For example, when the ROI is fed into another process as a seed, for example, where anatomical ROIs of the brain are fed into an automated tractography process for use as a seed ROI for automated computation of tracts between the seed ROIs.

In the case of anatomical images of the brain, the anatomical ROIs may include brain structures that include white matter tract(s), and/or gray matter, and/or a combination thereof.

As used herein, the term classifier and neural network may be interchanged.

As used herein, the term multi-modal neural network and neural network may be interchanged.

As used herein, the term component and path may be interchanged.

An aspect of some embodiments of the present invention relates to systems, an apparatus, methods, and/or code instructions (e.g., stored in a data storage device executable by one or more hardware processors) for automatic segmentation of three dimensional (3D) anatomical region(s) of interest (ROI) that include predefined anatomical structure(s) of a target individual. Multiple 3D images of a target individual depicting the predefined anatomical structure(s) are processed. Each 3D image is based on a different respective imaging modality. Exemplary predefined anatomical structure(s) include defined anatomical brain structures, and the prostate.

Optionally, instructions are generated according to the segmented ROIs, for example, by inputting the ROIs into another process (e.g., application, function, computing device). The instructions may be, for example, for automated tractography, for presentation on a display, for automated surgery on the segmented ROIs (e.g., executed by a surgical robot), for planning surgery on the segmented ROIs, and/or for assistance during surgery on the segmented ROIs (e.g., surgical guidance).

Optionally, a trained neural network, also referred to herein as a W-net architecture, computes the segmentation of one or more 3D ROIs that include the predefined anatomical structure(s). Each processing component of a plurality of processing components independently computes a respective intermediate output for a respective 3D image. Each processing component may perform contraction (also referred to herein as encoding-contracting path) and expansion (also referred to herein as decoding-expanding path) of the respective 3D image. The intermediate outputs, which are independently computed by the respective processing components are inputting into a common last convolutional layer, optionally a fully connected layer. The intermediate outputs may be merged (e.g., concatenated) before the last convolutional layer(s) of the trained neural network, optionally immediately prior to the input into the last convolutional layer. An indication of the segmented 3D ROI outputted by the fully connected layer(s) of the trained neural network includes the predefined anatomical structure.

The W-net architecture separately performs contraction and expansion of each image channel of the multi-modal images, and performs concatenation (i.e., merging) of the outputs of each separate contraction and expansion for input into the last common convolutional layer (e.g., fully connected layer(s)).

Alternatively, a trained neural network, referred to herein as a Y-net architecture, computes the segmentation of one or more 3D ROIs that include the predefined anatomical structure(s). Each 3D image of a certain imaging modality type (e.g., anatomical and DTI images) is processed by a distinct analysis component (i.e., encoding-contracting component) of the trained neural network (e.g., FCNN) that performs contraction, while synthesis is performed by a single common synthesis component (i.e., decoding-expanding component) of the trained neural network (e.g., FCNN) to which, at each synthesis step, are concatenated by skips the outputs of the analysis (i.e., contraction) steps for the corresponding analysis stage of the respective 3D image of the certain imaging modality type (e.g., 3D anatomical image and the 3D DTI image).

The Y-net architecture separately performs contraction of each image channel of the multi-modal images, and performs concatenation of the outputs of each separate contraction before performing expansion (of the concatenated data).

In one example, the W-net and/or Y-net trained neural network is applied to a 3D anatomical image of a brain of a target individual registered with a 3D diffusion tensor imaging (DTI) image of the brain indicative of principal direction of diffusion (PDD). The trained neural network outputs a 3D segmentation of one or more anatomical ROIs from the 3D anatomical image of the brain that include the predefined brain structures. One or more 3D white matter tract of the brain of the target individual may be computed by designating the segmented 3D anatomical ROI(s) as a seed of the DTI image of the brain. The computed 3D white matter tract(s) are outputted, optionally displayed on a display.

Moreover, in cases where the patient cannot collaborate during a functional MRI (fMRI) pre-operative mapping, for example because of a brain pathology affecting their ability to do so, the segmented anatomical ROI may be used as an alternative mapping. For example the pre-central gyms ROI segmented automatically as described herein, may serve as a mapping of the motor areas as would usually provided by fMRI when the patient is able to collaborate during the fMRI acquisition by performing the required motor tasks. The segmented ROI may be provided as a substitute for the region identified based on the fMRI (which requires cooperation by the patient), for input into a process, optionally an automated process, for example, a brain surgical planning process (e.g., brain surgery planning code instructions stored in a memory and executed by one or more hardware processors).

Optionally, the W-net and/or Y-net trained neural network includes a 3D multi-modal fully convolutional neural network (FCNN). The innermost portion of the FCNN may be designed for capturing content of the whole input volume.

Optionally, at least some components of the W-net implementation and components of the Y-net implementation are adaptations of components of the V-net architecture, as described herein. It is noted that the V-net architecture is designed for processing of a single 3D image based on one imaging modality, while the W-net and Y-net are designed for processing multiple types of 3D images, each of a different modality. As such, the W-net and Y-net represent novel and non-obvious architectures for 3D segmentation of multi-modal images using components designed for a single 3D image.

The components of the Y-net and/or W-net may be implemented as one or more of: 3D voxel filters (e.g., 5×5×5) of predefined dimensions, concatenation skips between parallel stages, residual skips in each stage, convolutions for down-sampling and deconvolutions for up-sampling. The number of 3D voxel filters at each stage of the first and second instances of the processing component of the neural network include, for example, 10, 20, 40, 80, and 160.

As used herein, the terms analysis path and encoding-contracting path (or encoder) may be interchanged.

As used herein, the terms synthesis path and decoding-expanding path (or decoder) may be interchanged.

Optionally, multiple 3D anatomical ROIs are segmented in parallel.

Exemplary 3D anatomical images include T1w magnetic resonance imaging (MRI) images of the brain containing data insufficient for imaging of one white matter tract. The 3D DTI image indicative of PDD includes a color map, optionally based on the red-green-blue (RGB) color scheme.

An aspect of some embodiments of the present invention relates to systems, an apparatus, methods, and/or code instructions (e.g., stored in a data storage device executable by one or more hardware processors) for training a W-net and/or Y-net neural network for outputting an automatic segmentation of 3D ROI(s) of a 3D anatomical image of a target individual that includes one or more predefined anatomical structures. A set of 3D anatomical images (each of a different imaging modality) that include the predefined anatomical structure(s), are received for each of multiple sample individuals. A 3D segmentation of one or more 3D anatomical ROI that include the predefined brain structure(s) is received for each of the anatomical images, for example, performed by a user based on standard manual methods. The W-net and/or Y-net is trained to identify the at least one predefined structure by computing a 3D segmentation of 3D anatomical ROI(s) that includes the predefined brain structure(s). The W-net and/or Y-net neural network is trained according to the set of registered 3D anatomical images each based on a different imaging modality of the sample individuals and the corresponding 3D manual segmentation of the 3D anatomical ROI(s) that include the predefined brain structure(s). The trained W-net and/or Y-net neural network is outputted for automatic 3D segmentation of 3D anatomical ROI(s) (that include the predefined brain structure(s)) of a new set of multi-modal registered 3D images of a new target individual.

The W-net and/or Y-net neural network is trained according to maximization of an objective function based on the set of multi-modal 3D images indicative of an imbalance between the number of voxels associated with multiple 3D anatomical ROIs segmented in parallel and background denoted by the voxels associated with the remaining tissue.

Optionally, prior to the training of the classifier, the multi-modal 3D images are cropped to predefined voxel dimensions defined by a cuboid bounding box including the manually segmented 3D anatomical ROI. The cuboid bounding box may be computed according to a reference cuboid bounding box automatically extracted from a no-gradient reference 3D image (e.g., DWI image of a brain) of the organ of the respective sample individual that includes the predefined anatomical structure(s).

Optionally, each 3D anatomical image is registered, optionally rigidly, with the corresponding 3D DTI image.

The Y-net and/or W-net implementations of a 3D multi-modal neural network, optionally a FCNN architecture, described herein may be implemented, for example, for the automatic segmentation of ROIs which are provided as input for example, as seeds into a process of tractography based on presurgical MRI scans. Each exemplary architecture implements a different approach to the combination of anatomical (e.g., T1w) information and white matter orientation patterns (e.g., color DTI maps).

The systems and/or apparatus and/or methods and/or code instructions (e.g., stored in a data storage device executable by one or more hardware processors) described herein provide a technical solution to the technical problem of automatically segmenting one or more 3D anatomical ROIs from a 3D anatomical image of a target individual. The 3D anatomical ROIs may be provided, for example, as input into code instructions that automatically compute one or more 3D white matter tracts of the brain (referred to as tractography"), for example, for in-vivo, pre-operative, and/or intra-operative mapping of connectivity of the brain of the target individual. In another example, the 3D anatomical ROIs may be provided as input into code instructions that automatically computes the prostate volume, map the different tissues of the prostate, including tumors and, accordingly, planning procedures and/or treatments on the prostate.

3D segmentation of anatomical ROIs is technically challenging, since the 3D anatomical ROIs, which have complex shapes, may appear differently in different people, for example, due to deformations and/or variations resulting from tumors, genetic anatomical variability, other abnormalities, and/or imaging artifacts.

The systems and/or apparatus and/or methods and/or code instructions described herein improve the technical field of automated 3D segmentation of 3D anatomical images, in comparison to other known automated 3D segmentation processes. The improvement may be provided, for example, in terms of accuracy of the 3D segmentation. The improvement may arise due to the multi-modal architecture of the classifier(s) described herein, that perform segmentation based on two or more anatomical imaging data acquired by two or more anatomical imaging modalities, optionally 3D imaging modalities. The improvement may arise due to the architectures of the multi-modal classifiers described herein, that include different implementations for integrating data from the two or more images acquired by the two or more imaging modalities.

The systems and/or apparatus and/or methods and/or code instructions described herein provide a technical advantage of a computational device that automatically computes the 3D anatomical ROIs and/or of the computational device that performs tractography mapping according to the 3D anatomical ROIs, by reducing the ROI delineation time to almost zero in particular in comparison to manual delineation of the ROIs which may take for example 1-3 hours, and/or provides fully automated tractography mapping without necessarily requiring human intervention and/or reducing human intervention.

The systems, apparatus, methods and/or code instructions (stored in a data storage device, executable by one or more hardware processors) described herein are directed to an improvement in computer-related technology, by improving the ability of computers to automatically segment predefined anatomical regions based on multi-modal images. Such 3D segmentation could only be properly performed by a human expert trained in the relevant medical field. Such manual segmentation is based on for example, instinct and/or experience. Other computer automated methods perform segmentation for a single 3D image, which results in a less accurate segmentation that performing multi-modal segmentation as described herein. Yet other computer automated methods perform segmentation independently for different 3D image, which results in a less accurate segmentation that performing multi-modal segmentation as described herein. However, it is noted that the systems, apparatus, methods and/or code instructions described herein are not merely a computer-implemented version of a mental process or intended to simply replicate or model human capability, but provide an improvement in the ability to segment complex anatomical structures which vary in location and/or geometric between individuals. The systems, apparatus, methods and/or code instructions described herein generate a new user experience, based on a new workflow pattern.

At least some systems, methods, apparatus, and/or code instructions described herein improve the medical and/or technological field of automated 3D segmentation of anatomical structures in 3D images, optionally complex anatomical structures such as in the brain. Using standard methods, a user (e.g., neuroradiologist, neurologist, neurosurgeon) manually examines the 3D images and manually performs the 3D segmentation. Such manual analysis is subjective, based on the individual user performing the segmentation, leading to inaccuracies which may arise from subjective experiences of the user performing the segmentation. Moreover, segmentation is technically challenging due to inter-subject variability, in which corresponding anatomical structures appears differently in different patients. Inter-subject variability may arise, for example, due to deformations of the anatomy, for example, due to tumors. The deformation may result in the target anatomical region being located at a different place than normally expected (e.g., shifted) and/or having a different shape than normally expected (e.g., due to deformation of its original shape by the tumor).

Reference is now made to FIG. 1, which includes images of different brains depicting the problem of inter-subject variability, to help understand technological improvements provided by some embodiments of the present invention. A calcarine sulcus 102A-D (shown in green in color images) is shown in four different brains. In another three different brains, tumors (pointed to by 104A-C) create deformations in the brain anatomy, causing that a precentral gyrus 106A-C looks different in each brain.

The automated 3D segmentation of anatomical ROIs by at least some of the systems, methods, apparatus, and/or code instructions described herein is not based on a simple coding of an existing manual process onto a computer. Rather, at least some systems, methods, apparatus, and/or code instructions described herein turn a subjective method into an objective, reproducible process based on the trained multi-modal classifier(s) code described herein. Inventors developed new steps that did not previously exist in the manual process, and do have not counterparts in the manual process, namely, the architecture(s) of the multi-modal classifier(s) code, training of the multi-modal classifier(s) code and/or execution of the trained multi-modal classifier(s) code for automatic 3D segmentation of 3D images. At least the trained multi-modal classifier(s) code described herein provides objective, reproducible 3D segmentation results, which are not available using standard manual processes.

The technical problem addressed by at least some of the systems, methods, apparatus and/or code instructions described herein is new, and specific for the technological context of 3D anatomical images. The technical problem related to 3D segmentation of anatomical objects of the 3D anatomical images arose only recently due to the technology of 3D medical imaging, and does not have a counterpart in the old physical world.

In addition to neuro-anatomical knowledge, significant amount of time is required for manual delineation of 3D structures, in particular for complex, non-planar, such as found in the brain, for example, the calcarine sulcus and/or the precentral gyrus. The technical problem of segmenting 3D structures is especially difficult considering the limited time often available for planning an urgent brain surgery.

Figure 2A:
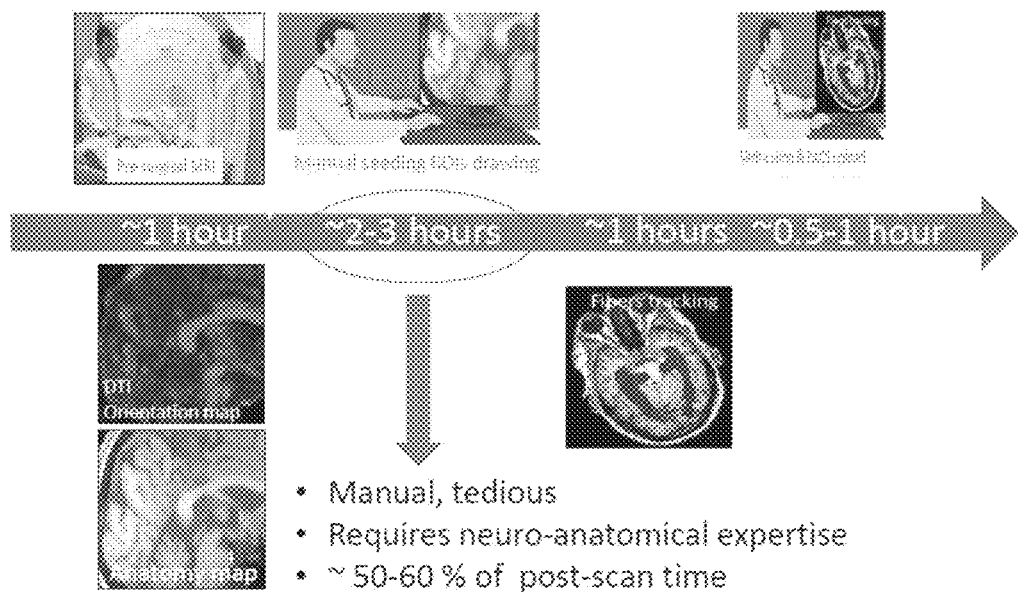
FIGS. 2A and 2B, which respectively depict a common practice workflow and an improved user experience workflow based on the automatic segmentation of one or more ROIs, in accordance with some embodiments of the present invention.
Figure 2B:
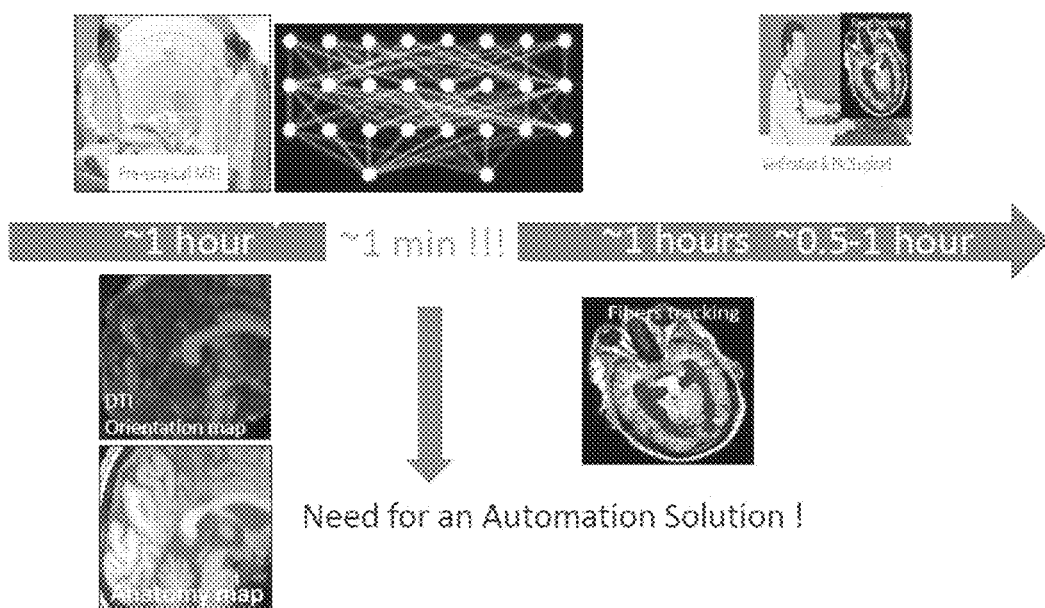

Reference is now made to FIGS. 2A and 2B, which respectively depict a common practice workflow and an improved user experience workflow based on the automatic segmentation of one or more ROIs, in accordance with some embodiments of the present invention. In particular, FIG. 2A-B relate to the case of segmentation of brain structure, but it is understood that the concept described applies to segmentation of other anatomical structures based on other multi-modal images. The common practice depicted with reference to FIG. 2A is performed manually by an expert. Very few individuals have the training and experience to accurate and correctly perform the manual segmentation. The manual segmentation is difficult, tedious, prone to inter-subject variability, prone to inaccuracy, and may take about 2-3 hours. In contrast, the automated segmentation workflow described with reference to FIG. 2B based on the automated segmentation by multi-modal classifier described herein (e.g., the Y-net and/or W-net neural networks) may be performed accurately and/or correctly by any user within a relatively short period of time (e.g., estimated at about 1 minute using commonly available standard computing resources).

White matter tractography has become an important tool for neuro-surgical planning and navigation as described with reference to Bick, A. S., Mayer, A. and Levin, N.: *From research to clinical practice: implementation of functional magnetic imaging and white matter tractography in the clinical environment. Journal of the Neurological Sciences* 312(1) 158-165 (2012) (hereinafter "Bick"). Generating accurate tracts in a brain deformed by a tumor may prove to be a challenging technical task. Beside a robust tractography algorithm, significant neuro-anatomical expertise is required to accurately delineate the fiber seeding ROIs. For example, an accurate tractography of the optic radiation requires the delineation of the Calcarine sulcus and the lateral geniculate nucleus (LGN). In addition to the neuro-anatomical knowledge, significant amount of time is required for the manual delineations of complex, non-planar 3-D structures like the Calcarine sulcus or the precentral gyrus in the motor cortex. Considering the limited amount of time often available for planning an urgent brain surgery, the automatic tools are badly needed for the delineation of anatomical ROIs.

The systems, apparatus, methods, and/or code instructions described herein that apply the 3D multi-modal statistical classifier for computation of the anatomical ROIs operate differently than other attempts of segmenting anatomical ROIs, in particular attempts at computing white matter tractography for the brain based on the segmented 3D anatomical ROIs. Some other known approaches are now discussed.

Most published approaches for tractography automation, for example, as described with reference to Tunç, B., Parker, W. A., Ingalhalikar, M. and Verma, R.: *Automated tract extraction via atlas based adaptive clustering. NeuroImage* 102 596-607 (2014) (hereinafter "Tunc"), and O'Donnell, L. J., Suter, Y., Rigolo, L., Kahali, P., Zhang, F., Norton, I., Albi, A., Olubiyi, O., Meola, A., Essayed, W. I. and Unadkat, P.: *Automated white matter fiber tract identification in patients with brain tumors. NeuroImage: Clinical* 13 138-153 (2017) (hereinafter "O'Donnell"), are based on the selection of relevant fibers following full-brain tractography, using registration to an atlas and clustering. Although these approaches avoid the need for ROI delineation, these approaches are less appropriate for probabilistic tractography methods. Seeding most of the brain is extremely time consuming with probabilistic tractography and is certainly unnecessary for retrieving the few major tracts typically considered in neuro-surgical navigation (motor, visual, and language). In contrast, at least some of the systems, apparatus, methods, and/or code instructions described herein automatically segment the ROIs, which may be provided as seeds into an automated tractography process (e.g., a processor executing the tractography code stored on a memory).

Other examples, such as described with reference to Goubran, M., Khan, A. R., de Ribaupierre, S., and Peters, T. M.: *Automated atlas-based seeding in cortico-spinal tractography. In: Proc. DTI Tractography for Neurosurgical Planning: A Grand Challenge*, 25-29. Toronto, Canada (2011) (hereinafter "Goubran"), and Scherrer, B., Suarez, R. O. and Warfield, S. K.: Automatic delineation of white matter fascicles by localization based upon anatomical spatial relationships. Proc. IEEE 10th International Symposium on Biomedical Imaging (ISBI), 1146-1149 (2013) (hereinafter "Scherrer"), considered the automatic delineation of the seeding ROI, but operate differently than the implementation(s) of the multi-modal classifier described herein. Goubran appears to relate to non-rigid registration with a single-subject atlas to automatically generate label-based seeds for tractography. The pre and post-central gyri labels from the atlas were used as seeds.

Scherrer appears to relate to ROIs localized using stable anatomical spatial relationships learned in the brain anatomy during a training phase with templates containing manually delineated ROIs. Fuzzy-sets theory and operators are used to fuse the spatial relationships between the ROIs and several anatomical landmarks. The learned spatial relationships are consequently applied to localize the ROIs in new subjects.

Other examples based on fully-convolutional neural networks (FCNN) with architectures that are different than the multi-modal classifier(s) described herein (e.g., Y-net, W-net), for example, are described with reference to Ronneberger, O., Fischer, P., Brox, T.: *U-net: Convolutional networks for biomedical image segmentation. Proc. Medical Image Computing and Computer-Assisted Intervention (MICCAI), Springer LNCS* 9351 234-241 (2015) (hereinafter "Ronneberger"), Çiçek, Ö., Abdulkadir, A., Lienkamp, S. S., Brox, T. and Ronneberger, O.: 3*D u-net: learning dense volumetric segmentation from sparse annotation. In: Medical Image Computing and Computer-Assisted Intervention (MICCAI), Springer LNCS* 9901 424-432 (2016) (hereinafter "Çiçek"), Dolz J, Desrosiers C, Ayed I B. 3*D fully convolutional networks for subcortical segmentation in MRI: A large-scale study. arXiv:*1612.03925, 2016. (hereinafter "Dolz"), Milletari, F., Navab, N. and Ahmadi, S. A.: *V-net: Fully convolutional neural networks for volumetric medical image segmentation. Proc. IEEE 4th International Conference on 3D Vision (3DV)*, 565-571 (2016) (hereinafter "Milletari"), and Eitel, A., Springenberg, J. T., Spinello, L., Riedmiller, M. and Burgard, W.: *Multimodal deep learning for robust rgb-d object recognition. In: IEEE/RSJ International Conference on Intelligent Robots and Systems (IROS)*, 681-687, 2015, (hereinafter "Eitel"), are implemented for complex image segmentation tasks, but using architectures that are different than the multi-modal classifier (e.g., W-net and/or Y-net) implementations described herein. Ronneberger appears to relate to a 2D FCNN, termed Unet, used for biomedical image segmentation. The architecture consists of a contracting path to capture context, followed by an expanding path that enables precise localization. This approach has been extended to 3D by Çiçek, whereby input volumes appear to be processed directly with 3D operations (i.e., 3D convolutions, 3D max pooling).

Dolz describes a 3D FCNN trained with 3D patches for subcortical segmentation in MRI. The main drawback of training with patches is the loss of spatial context, which is necessary for SROIs' segmentation.

A 3D FCNN, termed V-net, trained end to end, is described with reference to Milletari for the volumetric segmentation of prostate MRI, using the DICE coefficient as objective function to cope with the imbalance between foreground and background voxel numbers, as described with reference to Dice, L. R.: Measures of the amount of ecologic association between species. Ecology, 26(3) 297-302 (1945) (hereinafter "Dice"). The V-net of Milletari is designed to operate for a single 3D image input. No merger of multi-modal images is computed by the V-net.

Ma, L., Lu, Z., Shang, L., Li, H. *Multimodal convolutional neural networks for matching image and sentence. arXiv:*1504.06063 (2015) relates to a multi modal CNN that is defined and trained to match image and sentence.

Eitel, A., Springenberg, J. T., Spinello, L., Riedmiller, M. and Burgard, W.: *Multimodal deep learning for robust rgb-d object recognition. In: IEEE/RSJ International Conference on Intelligent Robots and Systems (IROS)*, 681-687 (2015) appears to relate to multi-modal data (RGB and depth information) for non-medical object recognition. For this purpose, two distinct convolutional networks, one for RGB and one for depth, were merged one layer before the output, which is different than processing volume data as described herein.

Chen, X., Ma, H., Wan, J., Li, B. and Xia, T., 2017, July. *Multi-view 3d object detection network for autonomous driving. In IEEE CVPR* (Vol. 1, No. 2, p. 3 (2017) relates to a multi modal network that used depth information from a LIDAR (Light Detection and Ranging) and an RGB image for 3D object detection for autonomous driving. The problem of segmenting 3D anatomical ROIs in 3D anatomical images is different than recognizing 3D objects for autonomous driving, for example, due to inter-subject variability which may arise from tumors, as described herein.

Zhang, W., Li, R., Deng, H., Wang, L., Lin, W., Ji, S. and Shen, D. *Deep convolutional neural networks for multi-modality isointense infant brain image segmentation. NeuroImage*, 108, pp. 214-224 (2015) (hereinafter "Zhang") and Nie, D., Wang, L., Gao, Y. and Sken, D. Fully convolutional networks for multi-modality isointense infant brain image segmentation. In *Biomedical Imaging (ISBI)*, 2016 IEEE 13th International Symposium on (pp. 1342-1345). IEEE. (2016) (hereinafter "Nie") relate to multi modal CNNs trained for infant brain segmentation by using T1-wieghted (T1w) scan, T2-weighted (T2w) scan and Fractional Anisotropy (FA) map. The architectures described by Zhang and Nie are different than the architectures of the multi-modal classifier described herein, for example, different than the W-net and Y-net architectures.

The human expert is limited in the ability to identify and integrate multiple characteristic patterns from several 3-D image sources. As such, at least some of the systems, apparatus, methods, and/or code instructions described herein, perform the task of integrating multiple 3D images that a human cannot perform, and/or perform such task with greater accuracy, and/or in an object manner over a human.

Figure 3:
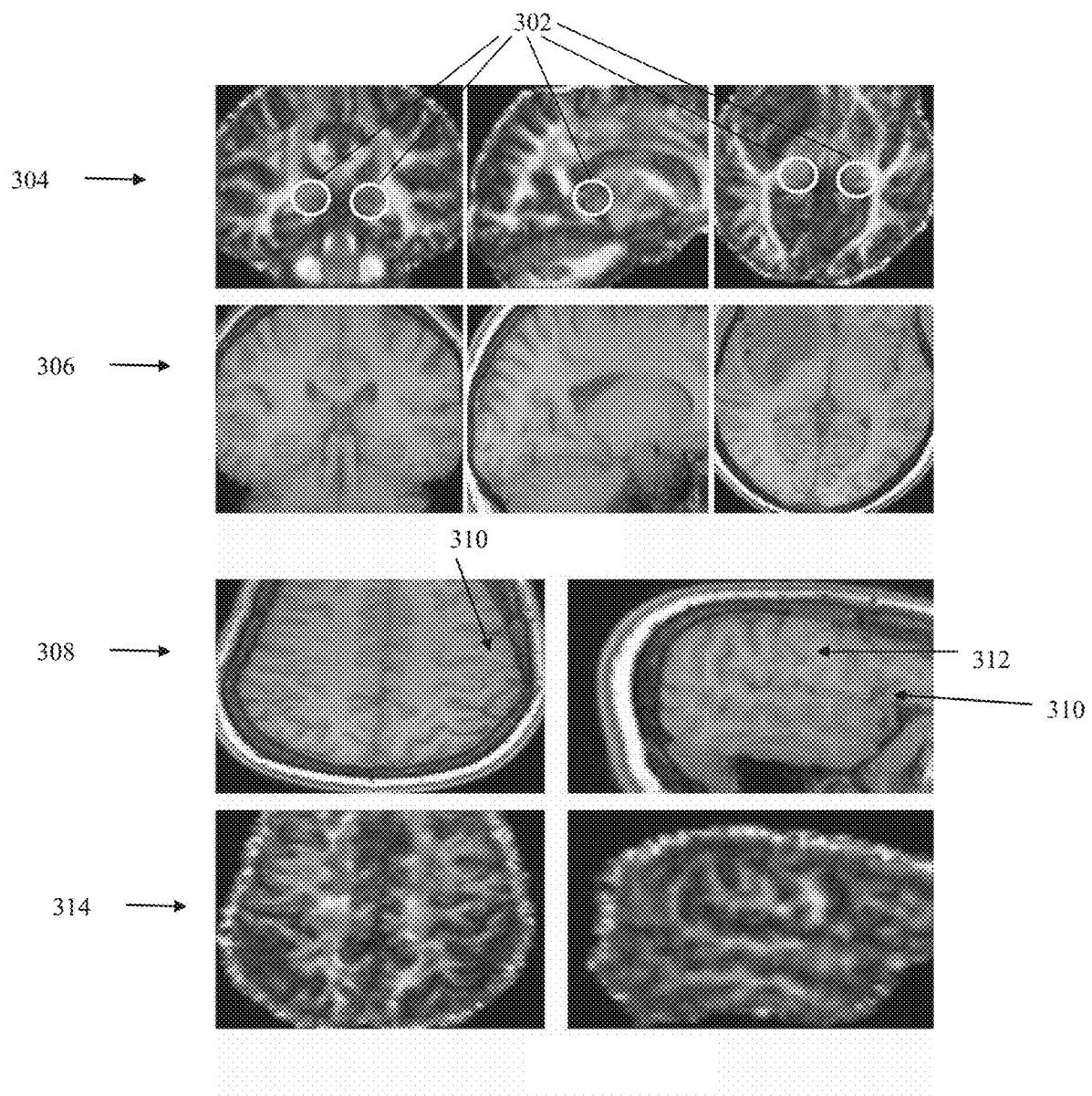
FIG. 3 is a schematic of two different images acquired from two different imaging modalities, depicting the difficulty in manually segmenting brain ROIs, to help understand the technical advantage of at least some embodiments of the present invention.

Reference is now made to FIG. 3, which is a schematic of two different images acquired from two different imaging modalities, depicting the difficulty in manually segmenting brain ROIs, to help understand the technical advantage of at least some embodiments of the present invention. Accurate manual delineation of tractography SROIs usually requires information from both an anatomical scan, typically T1w scan, and a principal direction of diffusion (PDD) map that is represented by an RGB volume, for example, as described with reference to Pajevic, S. and Pierpaoli, C. *Color schemes to represent the orientation of anisotropic tissues from diffusion tensor data: application to white matter fiber tract mapping in the human brain. Magnetic resonance in medicine*, 42(3), pp. 526-540 (1999). For example, The sROIs for the lateral geniculate nucleus (LGN) of the thalamus, which seeds anteriorly the optic radiation tract, are clearly localizable in the PDD color map 304 as indicated by circles 302. The position of the same LGN is more ambiguous in the T1w map 306. Conversely, the Precentral gyrus sROI, that seeds the motor tract, is better identified (312 shown in green overlay in color images, and line 310 shown as red in color images) in the T1w 308 scan than in the PDD 314.

The multi-modal classifier architectures described herein (e.g., Y-net, W-net) may be are different than the V-net architecture described with reference to Milletari. The multi-modal classifier architectures described herein are designed to integrate two or more different 3D images (e.g., obtained from different imaging modality devices) at different internal stages of the classifier. In contrast, even if the existing V-net architecture is used for pseudo multi-mode by feeding the images as separate channels (e.g., appending T1w and PDD maps into a four-channels volume: one for T1w and three for PDD), as performed by Inventors for the computation evaluation and described below with reference to the Examples section, at best, the images are fused before even entering the V-net, leaving no room for separate learning of the modalities before the fusion as occurs in the multi-modal classifier architectures described herein (e.g., Y-net, W-net).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 4:
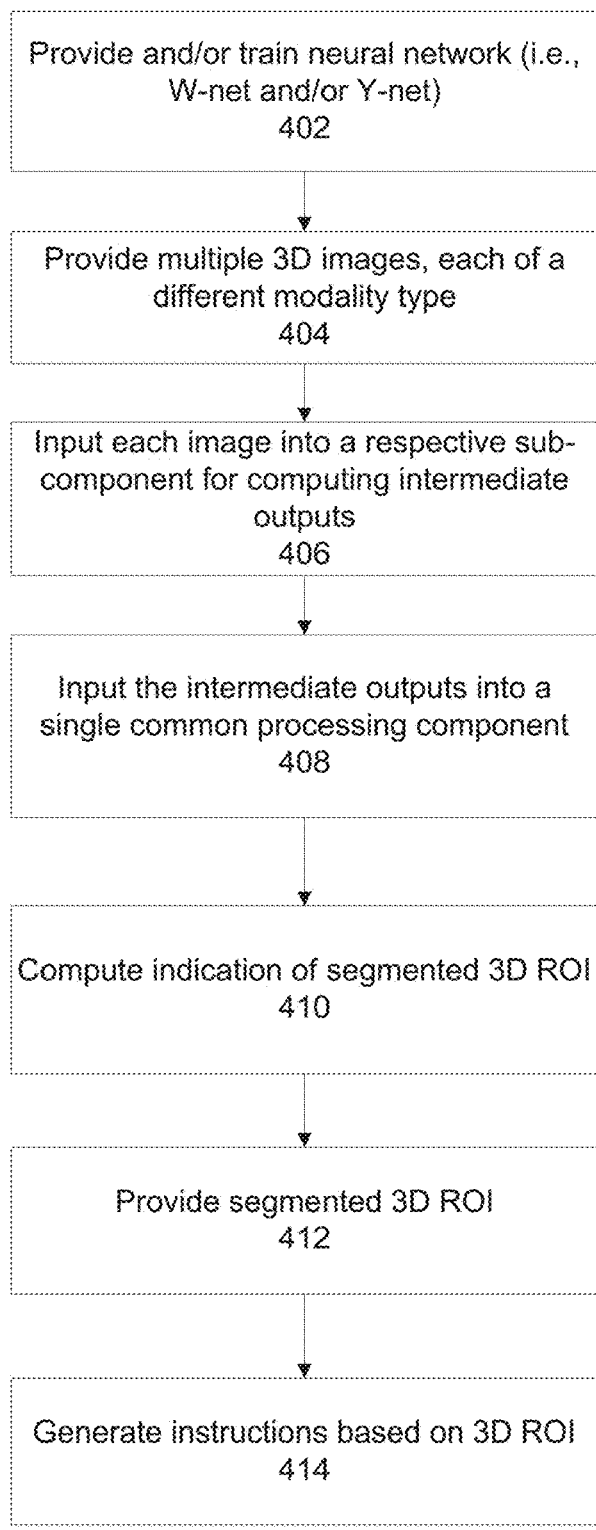
FIG. 4 is a flowchart of a method for automatic segmentation of 3D anatomical ROI by a multi-modal neural network that processes two or more images of different imaging modality types, in accordance with some embodiments of the present invention.
Figure 5:
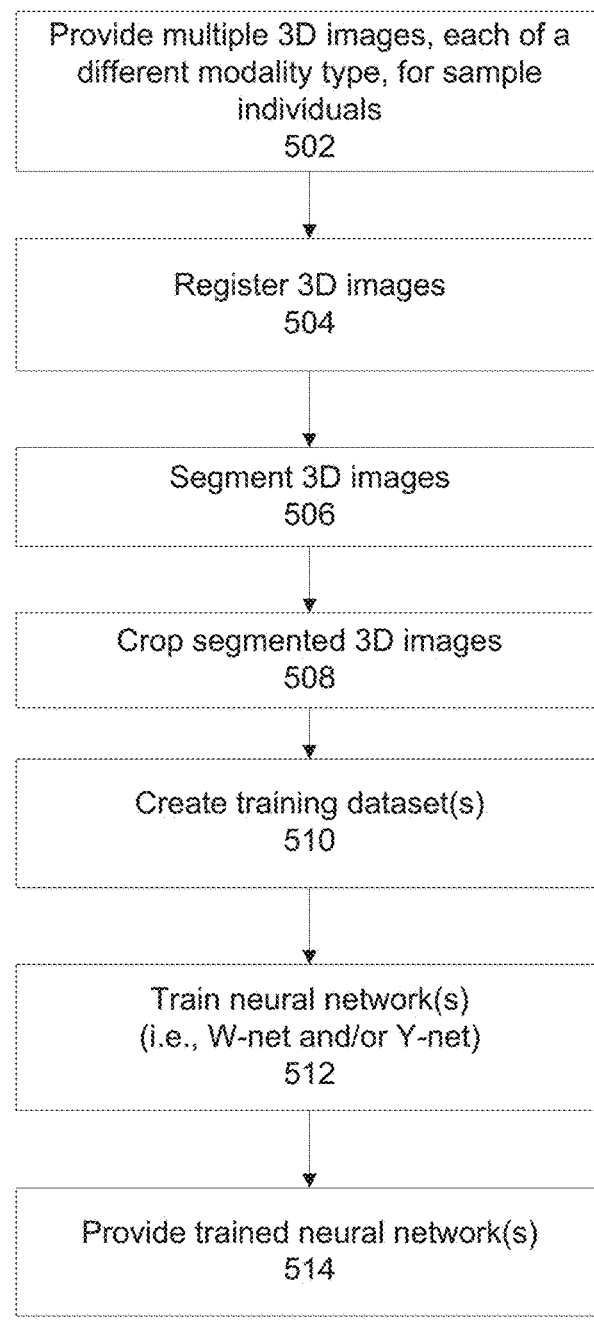
FIG. 5 is a flowchart of a method for training a multi-modal neural network for automatic segmentation of 3D anatomical ROIs according to an input of two or more images of different imaging modality types, in accordance with some embodiments of the present invention.
Figure 6:
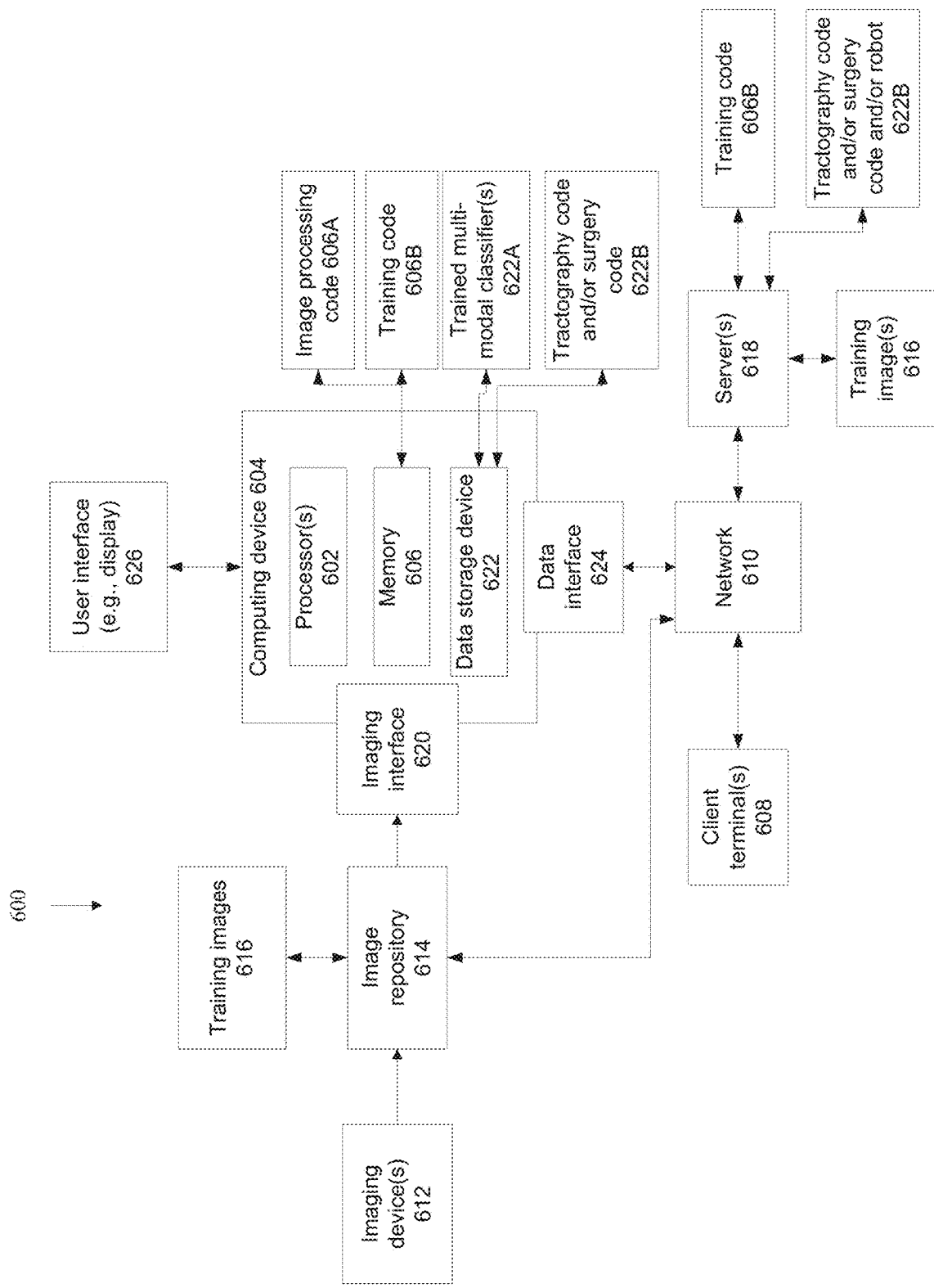
FIG. 6 is a block diagram of components of a system 600 for automatic segmentation of ROIs using the multi-modal neural network and/or training of the multi-modal neural network in accordance with some embodiments of the present invention.

Reference is now made to FIG. 4, which is a flowchart of a method for automatic segmentation of 3D anatomical ROI by a multi-modal neural network that processes two or more images of different imaging modality types, in accordance with some embodiments of the present invention. Reference is also made to FIG. 5, which is a flowchart of a method for training a multi-modal neural network for automatic segmentation of 3D anatomical ROIs according to an input of two or more images of different imaging modality types, in accordance with some embodiments of the present invention. Reference is also made to FIG. 6, which is a block diagram of components of a system 600 for automatic segmentation of ROIs using the multi-modal neural network and/or training of the multi-modal neural network in accordance with some embodiments of the present invention. System 600 may implement the acts of the method described with reference to FIG. 4 and/or FIG. 5, optionally by a hardware processor(s) 602 of a computing device 604 executing code instructions stored in a memory 606.

The W-net and/or Y-net may be implemented, for example, for computation of white matter tractography. In such application, the multi-modal 3D images include a 3D MRI anatomical image of a brain of a target individual, and a 3D diffusion tensor imaging (DTI) image of the brain indicative of principal direction of diffusion (PDD). The segmented 3D ROI includes predefined brain structure(s). The 3D anatomical image may include a T1w magnetic resonance imaging (MRI) image of the brain containing data insufficient for imaging of white matter tracts, and the 3D DTI image indicative of PDD includes a color map. One or more 3D white matter tracts of the brain of the target individual may be computed by designating the segmented 3D anatomical ROI(s) as a seed of the DTI image of the brain.

In another example, the W-net and/or Y-net are implemented for segmentation of an ROI that includes the prostate. In such application, the multi-modal 3D images may include a T2 weighted MRI scan, a diffusion weighted MRI, and a dynamic contrast enhanced scan.

Referring now back to FIG. 6, computing device 604 may be implemented as, for example, a client terminal, a server, a virtual server, a radiology workstation, a surgical workstation, a virtual machine, a computing cloud, a mobile device, a desktop computer, a thin client, a Smartphone, a Tablet computer, a laptop computer, a wearable computer, glasses computer, and a watch computer. Computing 604 may include an advanced add-on to a radiology workstation and/or a surgical workstation for presenting the segmented 3D ROIs and/or for computing additional medical data such as automated tractography using the ROIs as seeds and/or for performing automated surgery and/or assisting in a surgical procedure.

Computing device 604 may include locally stored software that performs one or more of the acts described with reference to FIG. 4 and/or FIG. 5, and/or may act as one or more servers (e.g., network server, web server, a computing cloud, virtual server) that provides services (e.g., one or more of the acts described with reference to FIG. 4 and/or FIG. 5) to one or more client terminals 608 (e.g., remotely located radiology workstations, remote surgical workstation, remote picture archiving and communication system (PACS) server, remote electronic medical record (EMR) server) over a network 610, for example, providing software as a service (SaaS) to the client terminal(s) 608, providing an application for local download to the client terminal(s) 608, as an add-on to a web browser and/or a medical imaging viewer application, and/or automated tractography application, and/or automated surgical application, and/or surgical planning application and/or surgical assist application, and/or providing functions using a remote access session to the client terminals 608.

Is it noted that the training of the multi-modal classifier (e.g., Y-net and/or W-net), and the application of the trained multi-modal classifier to multiple types of 3D anatomical images to segment ROI(s), may be implemented by the same computing device 604, and/or by different computing devices 604, for example, one computing device 604 trains the multi-modal classifier, and transmit the trained multi-modal classifier to a server device 604. Computing device 604 and/or another computing device in communication with computing device 604 receives the segmented ROIs and may execute code that uses the segmented ROIs to perform additional features, for example, automated tractography and/or surgical planning and/or surgical assistance and/or automated surgery.

Computing device 604 receives multiple types of 3D images, captured by one or more (optionally two or more different types of) anatomical imaging device(s) 612, also referred to herein as imaging modalities. Exemplary anatomical imaging device(s) 612 include: an ultrasound machine (e.g., 3D), a magnetic resonance imaging (MRI) device, a CT machine, and/or a nuclear imaging machine. Anatomical images captured by imaging machine(s) 612 may be stored in an image repository 614, for example, a storage server, a computing cloud, virtual memory, and a hard disk. Training images 616 may be created based on the captured anatomical images, as described herein.

Training images 616 are used to train the multi-modal classifier(s), as described herein. It is noted that training images 616 may be stored by a server 618, accessibly by computing device 604 over network 610, for example, a publicly available training dataset, and/or a customized training dataset created for training the multi-modal classifier(s), as described herein.

Anatomical images captured by imaging machine(s) 612 depict anatomical features and/or anatomical structures within a body portion of the target patient, for example, the brain, the chest, the abdomen.

Computing device 604 may receive the training images 616 and/or anatomical images from imaging device 612 and/or image repository 614 using one or more imaging interfaces 620, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 602 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 602 may include one or more processors (homogenous or heterogeneous), which may be arranged for parallel processing, as clusters and/or as one or more multi core processing units.

Memory 606 (also referred to herein as a program store, and/or data storage device) stores code instruction for execution by hardware processor(s) 602, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 606 may stores code instructions for implementing trained multi-modal classifiers 622A. Memory 606 stores image processing code 606A that implements one or more acts and/or features of the method described with reference to FIG. 4, and/or training code 606B that executes one or more acts of the method described with reference to FIG. 5.

Computing device 604 may include a data storage device 622 for storing data, for example, a trained multi-modal classifiers 622A (as described herein), and/or training images 616. Data storage device 622 may be implemented as, for example, a memory, a local hard-drive, a removable storage device, an optical disk, a storage device, and/or as a remote server and/or computing cloud (e.g., accessed over network 610). It is noted that trained multi-modal classifiers 622A, and/or training images 616 may be stored in data storage device 622, with executing portions loaded into memory 606 for execution by processor(s) 602. Data storage device 622 may store tractography code and/or surgery code 622B that uses the ROIs automatically segmented by the trained multi-modal classifiers, for example, for automated tractography, for planning a surgery, for automated surgery, and/or for assistance with the surgery. Alternatively, tractography code and/or surgery code 622B is stored on a server(s) 618 in communication with computing device 604, for example, a surgery workstation.

Computing device 604 may include data interface 624, optionally a network interface, for connecting to network 610, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 604 may access one or more remote servers 618 using network 610, for example, to download updated training images 616 and/or to download an updated version of image processing code 606A, training code 606B, and/or the trained multi-modal classifier(s) 622A.

Computing device 604 may communicate using network 610 (or another communication channel, such as through a direct link (e.g., cable, wireless) and/or indirect link (e.g., via an intermediary computing device such as a server, and/or via a storage device) with one or more of:

Client terminal(s) 608, for example, when computing device 604 acts as a server providing image analysis services (e.g., SaaS) to remote radiology terminals, for analyzing remotely obtained anatomical images, and/or providing surgical planning services to remote surgical terminals based on the ROIs segmented from the anatomical images.

Server 618, for example, implemented in association with a PACS, which may storage large numbers of anatomical images for analysis, for example, captured by an imaging machine of a radiology clinic.

Server 618, for example, implemented in association with a surgical workstation, for performing automated tractography, planning surgery, surgical assistance, and/or automated surgery (e.g., surgical robot).

Anatomical image repository 614 that stores training images 616 and/or anatomical images outputted by imaging device 612.

It is noted that imaging interface 620 and data interface 624 may exist as two independent interfaces (e.g., two network ports), as two virtual interfaces on a common physical interface (e.g., virtual networks on a common network port), and/or integrated into a single interface (e.g., network interface).

Computing device 604 includes or is in communication with a user interface 626 that includes a mechanism designed for a user to enter data (e.g., patient data) and/or view the segmented ROI(s). Exemplary user interfaces 626 include, for example, one or more of, a touchscreen, a display, a keyboard, a mouse, and voice activated software using speakers and microphone.

Referring now back to FIG. 4, at 402, the multi-modal neural network(s) is selected, provided, and/or trained. For example, both Y-net and W-net may be selected, or one of Y-net and W-net may be selected, for example, according to computational evaluation of the architecture the provides best results for the predefined anatomical structures and/or for the type of image modality.

Multiple instances of the Y-net and/or W-net architectures may be trained. Each instance may be trained to process a certain combination of imaging modality types of 3D anatomical images, for example, MRI images (e.g., T1w) and principal direction of diffusion maps (PDD) (e.g., color, optionally 3 channels). In another example, each instance is trained for a certain predefined anatomical structures, for example, lateral geniculate nucleus (LGN) of the thalamus, calcarine sulcus in the occipital lobe, precentral-gyrus (posterior frontal lobe), brain stem, Wernicke area, Broca area, motor tract, sensory tract, arcuate fasciculus, optic radiation tract, other white matter tracts of the brain and/or gray matter structures of the brain, and combinations of the aforementioned, and prostate tissues including lesions and/or tumors.

The instance of the neural network may be selected from multiple available neural network instances. The selection may be performed manually by the user (e.g., via a user interface, for example, displaying a menu and/or icons of available neural networks). The selection may be performed automatically by code that determines the combination of imaging modalities of the input images and/or according to clinical indication (e.g., type of surgery being planned). The automated analysis may be, for example, based on an analysis of the image itself, and/or an analysis of metadata of the image, and/or according to data associated with the image series (e.g., obtained from a PACS server, DICOM data, and/or electronic medical record).

An exemplary method of training the neural network(s) is described with reference to FIG. 5.

Figure 7:
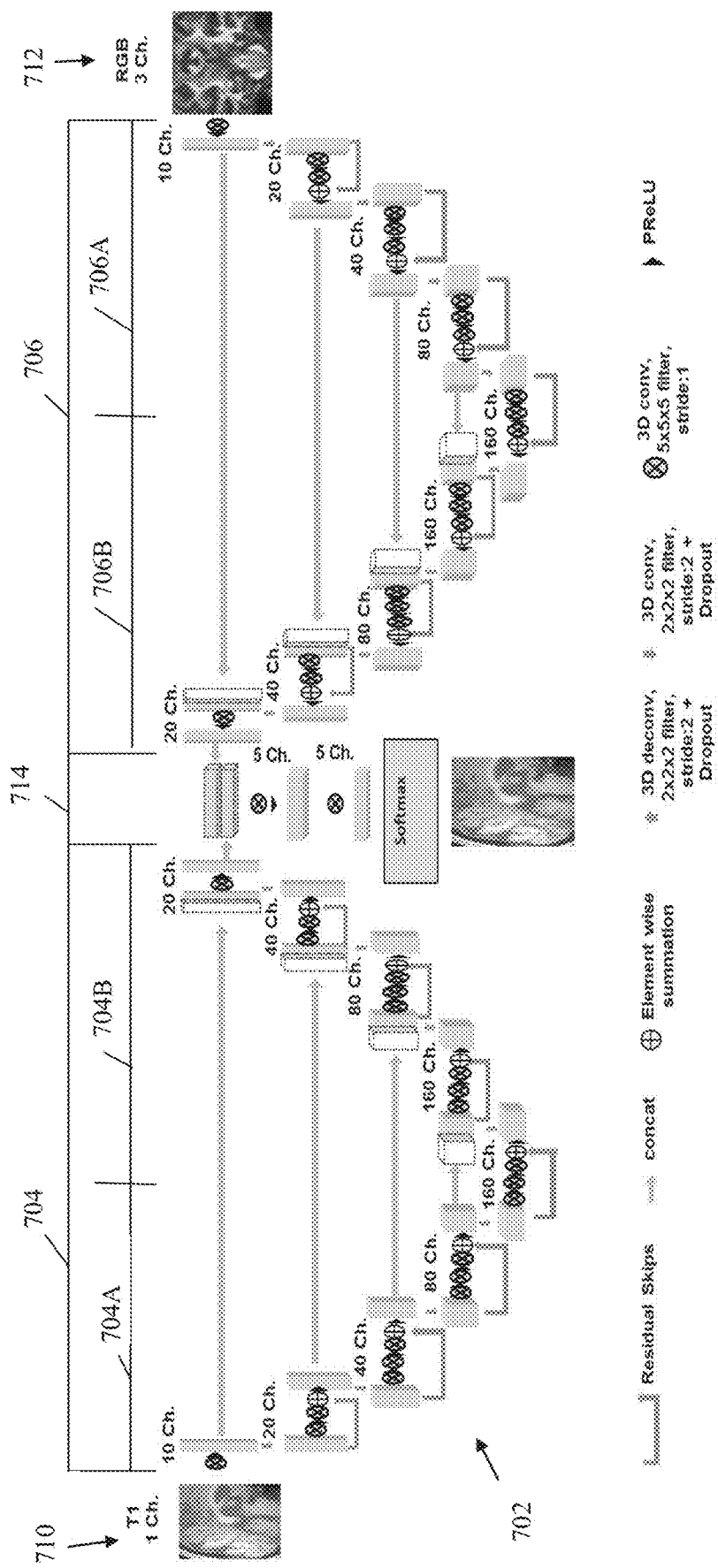
FIG. 7, which is a schematic depicting an exemplary W-net architecture 702, in accordance with some embodiments of the present invention.

Reference is now made to FIG. 7, which is a schematic depicting an exemplary W-net architecture 702, in accordance with some embodiments of the present invention. Y-net 702 is designed for segmentation of anatomical structure(s) based on independently processing each data modality of multiple images based on different imaging modalities and merging the streams before the last convolutional layer (e.g., fully connected layer(s)).

The architecture of the W-net 702 includes multiple processing component 704 706. For simplicity and clarity of explanation two processing components 704 706 are illustrated, but it is to be understood that three or more processing components may be implemented. Each processing independently computes a respective intermediate output for a respective 3D image of a different imaging modality type. 3D image 710 (e.g. T1 MRI image) is fed into processing component 704, and 3D image 712 (e.g., three color channel PPD) is fed into processing component 706. The intermediate outputs inputted into a common last convolutional layer 714, optionally a fully connected layer. The intermediate outputs may be merged before the common last convolutional layer 714. The common last convolutional layer outputs an indication of the segmented 3D ROI(s), optionally for presentation on a display and/or for input into another code for further processing (e.g., automated surgery, automated tractography).

Each processing component 704 706 includes an encoding-contracting path 704A 706A for capturing context based on multiple computed feature channels, and a decoding-expanding path 704B 706B for localization based on the computed features. Features extracted from stages of the encoding-decoding path are forwarded to corresponding stages of the decoding-expanding path for gathering fine grained detail that would otherwise be lost in compression computations of the encoding-contracting path.

The number of feature channels doubles for each sequential stage of the encoding-contracting path, and is halved for each sequential stage of the decoding-expanding path. For example, the number of 3D voxel filters (each corresponding to a respective feature channel) at each stage of each instance of the common component are: 10, 20, 40, 80, and 160.

Optionally, each processing component includes multiple stages each operating at a different resolution.

Each stage includes one or more convolution layers. Each stage learns a respective residual function. The residual function is learned based on input of each stage being processed by the convolutional layer(s) of the respective stage, and added to the output of the last convolutional layer of the respective stage for learning the residual function.

Convolutional operations at each stage are performed using volumetric kernels of a common size. The resolution of the respective 3D image is reduced as data of the respective 3D image proceeds through different stages along the encoding-compression path.

The number of feature channels doubles at each state of compression as the resolution is reduced. Features computed in the deepest layer perceive the whole ROI at once based on computation from data having a spatial support larger than the at least one predefined anatomical structure.

It is noted that different architectures of the processing component (when implemented for a single 3D image) may be implemented in the multi-modal neural network architectures (i.e., Y-net, W-net) described herein. The multi-modal neural network architectures integrate the outputs of multiple processing components, each processing a single type of imaging modality, as described herein. For example, the V-net neural network described with reference to Milletari. As discussed herein, the architecture designed for multiple 3D images of different imaging modalities may be based on modification of components designed for single 3D images, which is a novel and non-obvious technical challenge solved by Inventors.

Optionally, each processing component 704 706 of the W-net architecture 702 is based on a respective v-shaped FCNN, for example, based on the V-net architecture described with reference to Milletari and/or other architectures.

Optionally, each processing component 704 706 is implemented as 3D filters based on predefined voxel dimensions (e.g., 5×5×5 or other dimensions), concatenation skips between parallel stages, residual skips in each stage, convolutions and deconvolutions for down and up-sampling, respectively (optionally by 2×2×2 filters with stride=2, or other values for the filters and other stride values).

In comparison to the classical V-net, the number of filters at each stage may reduced from [16, 32, 64, 128, 256] to, for example, [10, 20, 40, 80, 160]. The filter reduction maintains about the same total number of parameters as in the original published V-net to allow for a fair comparison in the Example section described below. Restricting the number of parameters reduces computations resources (e.g., processing time, processor utilization, memory storage requirement) of the training phase. The total number of parameters for the straightforward Vnet extension (as used in the experiments, and described in the Examples section below) and the W-net is approximately 65 million and approximately 50 million respectively.

Figure 8:
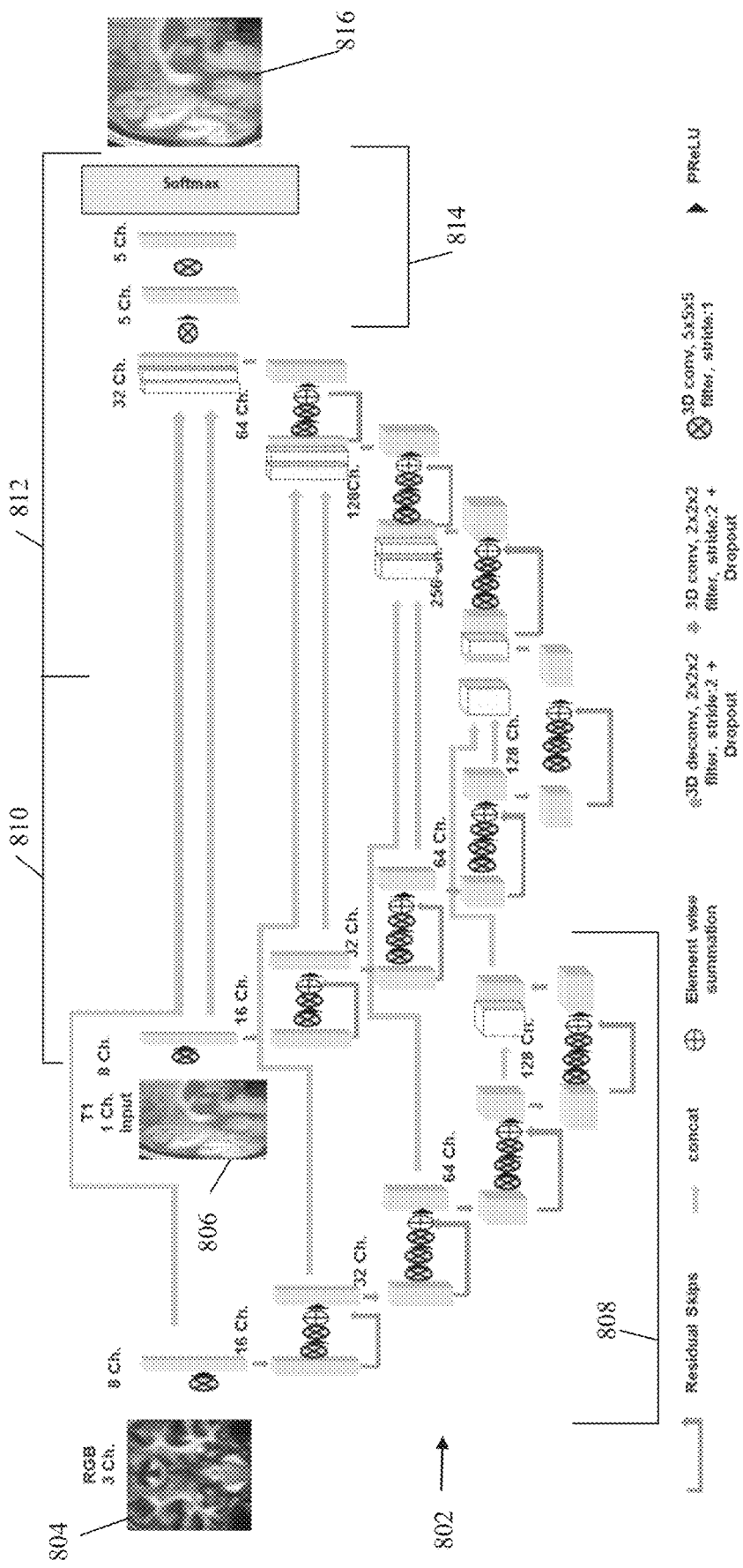
FIG. 8 is a schematic depicting an exemplary Y-net architecture of the multi-modal neural network, in accordance with some embodiments of the present invention.

Reference is now made to FIG. 8, which is a schematic depicting an exemplary Y-net architecture 802 of the multi-modal neural network, in accordance with some embodiments of the present invention. Y-net 802 is designed for segmentation of anatomical structure(s) based on enforcing multimodality of multiple images based on different imaging modalities from the beginning of synthesis, through the stages, in accordance with some embodiments of the present invention.

Each 3D image 804 806 of a different modality type (e.g., three channel color PPD and T1 MRI), is independently processed by a respective encoding-contracting component 808 810. For example, image 804 is inputted into encoding-contracting component 808, and image 806 is inputted into encoding-contracting component 810. Each encoding-contracting component 808 810 computes a respective intermediate-output. The multiple intermediate-outputs are fed into a single common decoding-expanding component 812. Each stage of the single common decoding-expansion component 812 may be concatenated by skips of outputs generated by each corresponding stage of each respective encoding-contracting component 808 810.

It is noted that there may be three or more encoding-contracting components for processing three or more types of imaging modalities. The depicted implementation of two encoding-contracting components is exemplary and not necessarily limiting.

Each encoding-contracting component 808 810 captures context from the respective 3D image based on feature channels computed by each respective stage. The common decoding-expanding component 812 performs localization based on the computed features.

The output layer 814 of the single common decoding-expanding path 812 provides an indication of the segmented 3D ROI(s) that includes the predefined anatomical structure(s), for example, for presentation on a display, for example, shown as image 816.

Optionally, each encoding-contracting component 808 810 and/or the common decoding-expanding component 812 is implemented as 3D filters based on predefined voxel dimensions (e.g., 5×5×5 or other dimensions), concatenation skips between parallel stages, residual skips in each stage, convolutions and deconvolutions for down and up-sampling, respectively (optionally by 2×2×2 filters with stride=2, or other values for the filters and other stride values).

Optionally, the number of filters at each stage of the analysis path, i.e., encoding-contracting components 808 810 is [8, 16, 32, 64, 128], or other values and/or other number of filters may be used. Optionally, the number of filters at each stage of the synthesis path, i.e., common decoding-expanding component 812 is [256, 128, 64, 32], or other values and/or other number of filters may be used.

The filters are selected to maintains about the same total number of parameters as in the W-net and original published V-net to allow for a fair comparison in the Example section described below. The total number of parameters for the Y-net is approximately 48 million.

Different architectures of the common encoding-contracting component and/or the single common decoding-expanding component (when implemented for a single 3D image) may be implemented. For example, encoding and/or decoding components described for processing single images may be used in the multi-modal architecture described herein, by using multiple instances of the encoder and/or decoder, each processing a single type of image modality, and fusing the intermediate outputs for input into a common component designed for multi-modal processing, as described herein. An example of an architecture of the encoder and/or decoder used for single images is found, for example, with reference to the V-net neural network described with reference to Milletari. As discussed herein, the architecture designed for multiple 3D images of different imaging modalities may be based on modification of components designed for single 3D images, which is a novel and non-obvious technical challenge solved by Inventors. As discussed in the Examples section, Inventors discovered that the multi-modal architecture provides improved results over architectures designed for single images.

Referring now back to FIG. 4, at 404, multiple 3D images, each of a different modality type, are received.

Multiple 3D images of a target individual are received. Each 3D image includes the predefined anatomical structure. Each 3D image is based on a different respective imaging modality. It is noted the same machine may created multiple images each of a different modality, for example, different types of MRI images. The segmentation of the 3D ROI(s) that includes the predefined anatomical structure is computed by the neural network, as described herein. Optionally, the multiple 3D images are registered to one another, for example, by an automated process and/or manual process. The segmentation of the 3D ROI is computed for the registered images, and may be presented on one or more (optionally each one) of the 3D images.

The images may be obtained, for example, from a PACS server, an EMR server, from the anatomical imaging device(s), and/or from a storage device (e.g., portable storage medium, storage server). For example, anatomical images are automatically sent to analysis after capture by the imaging modality and/or once the images are stored.

At 406, each image is inputted into a corresponding sub-component of the neural network. Each sub-component of the neural network computes a respective intermediate output.

For the W-net, each respective 3D image is inputted into the corresponding respective processing component. As discussed herein, for the W-net, each processing component may be implemented as an encoding-contracting path and a decoding-expanding path. The encoding-contracting path may be for capturing context based on computed feature channels. The decoding-expanding path may be for localization based on the computed features.

For the Y-net, each respective 3D image is inputted into the corresponding respective encoding-contracting component.

At 408, the multiple intermediate outputs computed by the multiple sub-components are inputted into a single common processing component. The intermediate outputs may be merged prior to input into the single common processing component. The merged intermediate outputs are inputted into the single common processing component.

For the W-net, the intermediate outputs of the encoding-contracting path and decoding-expanding path are inputted into a common last convolutional layer(s), optionally a fully connected layer(s).

For the Y-net, the intermediate outputs of the encoding-contracting components are inputted into a single common decoding-expanding component.

At 410, an indication of the segmented 3D ROI(s), that includes the predefined anatomical structure, is computed. The segmented 3D ROI(s) may be computed for one or more of the 3D images, optionally for each of the 3D images.

The indication of the segmentation may be computed and/or outputted by the last convolutional layer(s) of the Y-net and/or W-net.

The indication of the segmentation may be represented, for example, by color coding of pixels of the image(s) corresponding to the segmented ROIs, by geometrical shapes defining the border(s) of the segmented ROI(s), and/or by coordinates of the pixels of the image(s) corresponding to the segmented ROIs.

Exemplary segmented ROIs computed for images of the brain include: lateral geniculate nucleus (LGN) of the thalamus, calcarine sulcus in the occipital lobe, precentral-gyrus (posterior frontal lobe), brain stem, Wernicke area, Broca area, motor tract, sensory tract, arcuate fasciculus, optic radiation tract, at least one white matter tract, at least one gray matter structure, and a combination of the aforementioned.

Exemplary segmented ROIs may include prostate tissue, including tumors and/or lesions of the prostate.

At 412, the indication of the segmented 3D ROI(s) is provided. The indication of the segmented 3D ROI(s) may be presented on a display, stored in a data storage device (e.g., in a PACS server, and/or EMR of the subject), and/or forwarded to another process (e.g., application, server, workstation) for further processing.

At 414, instructions are generated according to the segmented ROI(s). The instructions may be code for execution by processor(s), and/or the instructions may be manual instructions for execution by a user. Manual instructions may be presented to a user, for example, as text, as a movie, as an animation, and/or as audio.

The automated instructions may include, for example, for:
Automatic computation of tractography using the segmented ROI(s) as seeds. For example, computing an optic radiation tract using the LGN and calcarine sulcus segmented ROIs as seed ROIs, computing a motor tract using the precentral-gyrus and brain stem segmented ROIs as seed ROIs, and computing an arcuate tract using the Wernicke and Broca segmented ROIs as seed ROIs.
Automatic surgery by a surgical robot. For example, automated excision o the segmented ROI(s) by the surgical robot.
Surgical planning by a surgical planning application. For example, assisting the surgeon with planning surgical access to the segmented ROI(s).
Real time surgical assistance by a surgical assistance application. For example, real time navigation of surgical instruments for operating on the segmented ROI(s).

It is noted that the manual instructions may be for manual execution of the above mentioned automated tasks.

Referring now back to FIG. 5, at 502, sets of anatomical images are provided for each of multiple sample individuals. Each set of anatomical images include two or more 3D images created based on different imaging modalities. The images of each set depict one or more predefined anatomical structures of the sample.

At 504, the anatomical images of each set may be registered. Registration may be performed based on automated and/or manual processes. Registration may be rigid.

At 506, a 3D segmentation of one or more anatomical ROIs that each include the predefined anatomical structure(s) are provided. Segmentation may be performed for one or more, optionally for each one, of the registered 3D images of the respective set of images. As discussed below in the Examples section, the anatomical structures may be difficult to delineate for some imaging modalities. In such cases in which only some images of the set are segmented, the trained neural network is still an able to accurately segment the 3D images, as described in additional details in the Examples section below.

3D segmentation may be performed manually by a trained user, according to standard medical practice. For example, using a graphical user interface (GUI) to draw a border around the anatomical structure(s), and/or shade-in the anatomical structure(s), and/or other methods of selection of pixel and/or voxels associated with the anatomical structures(s).

3D segmentation may be automatically performed by code, individually on each 3D image. The automatic segmentation may be evaluated by the user and optionally manually corrected.

At 508, the images may be cropped to a window that includes the segmented ROI(s). The window size may be selected to be of a uniform size to include the segmented ROI(s) in all images. The cropping is designed to limit running time and/or memory requirements. It is noted that cropping may not necessarily be required with sufficient computational resources and/or sufficient memory resources are available to process the entire non-cropped images within a reasonable time.

For example, for the case of ROI(s) of brain structures, a cuboid bounding box, circumscribing the brain may be automatically extracted from B0 (i.e., no-gradient DWI image) and used as reference for the cropping window positioning on the co-registered PDD and T1w images. The obtained cropping window contains all the required SROIs while removing about half of the brain volume. Additional exemplary details of cropping are described in the Examples section below.

At 510, one or more training datasets are created for training one or more neural networks. Each training dataset includes set of anatomical images with segmented ROIs, clustered according to a common feature, for example, a common anatomical structured depicted in the segmented ROIs and/or a common combination of imaging modality types (e.g., T1 MRI and color PPD).

For example, multiple training dataset are created, each for a different brain structure, for example, lateral geniculate nucleus (LGN) of the thalamus, calcarine sulcus in the occipital lobe, precentral-gyrus (posterior frontal lobe), brain stem, Wernicke area, Broca area, other white matter tracts of the brain and/or gray matter structures of the brain, and prostate tissues and/or tumors.

At 512, one or more neural networks, including Y-net and/or W-net architectures, are trained according to the created training dataset(s).

The multi-modal neural network(s) are trained to compute the anatomical ROI(s) that include the predefined anatomical structure(s) for an input of a new set of registered 3D images of different imaging modality types.

The W-net and/or Y-net neural network may be trained according to maximization of an objective function based on the registered 3D images indicative of an imbalance between the number of voxels associated with 3D anatomical ROIs segmented in parallel and background denoted by the voxels associated with the remaining tissue external to the anatomical ROIs. The objective function denoted MeanDice is described in additional detail herein.

It is noted that the ROIs may represent a small part of the total anatomical part depicted in the image, for example, a small part of the total brain volume. In such cases, an imbalance exists between the number of voxels belonging to the desired anatomical ROIs and the remainder of the anatomical body portion such as brain (i.e., background). The Dice coefficient described by Milletari may prove a better solution in this imbalanced scenario than the classical weighted cross-entropy.

The Dice coefficient described by Milletari is defined for a single label. In contrast, the multi-modal neural network described herein is designed to process multiple labels, for example, 4 labels in the case of segmenting brain structures. At least four labels are necessary for each tract of the brain: two sROIs defining the tract extremities, repeated in each brain hemisphere (left and right). A multi-label extension is given by the mean of the individual Dice coefficients for the foreground labels, for example, as described with reference to Fidon, L., Li, W., Garcia-Peraza-Herrera, L. C., Ekanayake, J., Kitchen, N., Ourselin, S., and Vercauteren, T. *Generalised Wasserstein Dice score for imbalanced multi-class segmentation using holistic convolutional networks. arXiv:* 1707.00478 (2017).

The multi-label formulation of the Dice coefficient may be implemented for the simultaneous segmentation of several anatomical ROIs. The proposed confidence, term herein Mean Dice, denotes the mean of the Dice coefficient for each foreground label, is computed according to Equation 1:

$$MeanDice = \frac{1}{L}\sum_{l=1}^{L} D_l \quad \text{Equation (1)}$$

where $$D_l = \frac{2\sum_{i}^{N} p_{li} g_{li}}{\sum_{i}^{N} p_{li}^2 + \sum_{i}^{N} g_{li}^2} \quad \text{Equation (2)}$$

L denotes the number of foreground labels,
N denotes the number of voxels,
$p_{li} \in [0,1]$ denotes the softmax score for label l in voxel i, and
$g_{li}$ denotes the binary ground truth for label l in voxel i.
MeanDice ($\in [0,1]$) is computed between a binary map (the ground truth) and a soft map (the prediction), which provides more information for accurate score computation in comparison to a crisp Dice score in which the soft map is thresholded before its computation.

At 514, the trained multi-modal neural network(s) are provided. The trained neural network(s) may be locally stored by the computing device, and/or forwarded to the computing device when the training is performed by another device.

Various embodiments and aspects of the systems, apparatus, methods, and/or code instructions as delineated hereinabove and as claimed in the claims section below find experimental and/or calculated support in the following examples.

EXAMPLES

Reference is now made to the following examples, which together with the above descriptions illustrate some embodiments of the systems, apparatus, methods, and/or code instruction described herein in a non limiting fashion.

Inventors performed experiments as described herein, in which both of the exemplary architectures of the statistical classifier described herein are successfully validated on real tumor resection candidates for 3D segmentations of seeding ROIs (SROI) for the motor tract, the arcuate fasciculus, and the optic radiation tract. The multi-modal architecture of the statistical classifier(s) described herein is compared to the state-of-the-art V-net architecture. The results of the computational evaluations described herein indicate that sROIs may be automatically computed by the multi-modal classifier(s) described herein, which may improve efficiency of pre-surgical tractography mapping, without necessarily compromising quality of the tractography.

The terms Y net and W net denote two exemplary implementations of the multi-model architecture of the statistical classifier(s), as described herein.

The Data

The dataset used for the experiments included 75 cases referred to the Chaim Sheba Medical Center (Tel-Hashomer, Israel) for brain tumor removal surgery. For each case a high resolution T1w anatomical scan ($1 \times 1 \times 1$ mm$^3$, no contrast injection) was available together with a rigidly co-registered PDD RGB map ($1 \times 1 \times 2.6$ mm$^3$ resliced to $1 \times 1 \times 1$ mm$^3$), where mm$^3$ denotes a cubic millimeter. The scans were acquired on a 3T Signa machine (GE healthcare, Milwaukee). The DWI protocol comprised 64 gradient directions at $B_0=1000$ and 1 scan at $B_0=0$. Tensor fitting and PDD maps were computed with the MrDiffusion toolbox (e.g., available at www(dot)web(dot)stanford(dot)edu/group/vista/cgi-bin/wiki/index(dot)php/MrDiffusion) for Matlab.

Ground-Truth Generation

The ground-truth (GT) for the sROIs was generated before the experimental evaluation for the actual pre-surgical planning of the 75 cases in the dataset. In this context fMRI information was generally available for most of the cases, allowing for a more confident manual segmentation of the cortical sROIs.

The sROIs for motor, optic radiation and arcuate tracts were manually segmented in 3-D for both hemispheres of each brain by an expert in neuro-anatomy and verified by a senior neuroradiologist (GT) using the MrDiffusion GUI (e.g., available at www(dot)web(dot)stanford(dot)edu/group/vista/cgi-bin/wiki/index(dot)php/MrDiffusion). For each tract, 2 sROIs were defined as follows:

The Optic Radiation Tract

The optic radiation connects the lateral geniculate nucleus (LGN) of the thalamus to the calcarine sulcus in the occipital lobe. The optic radiation is best reconstructed using probabilistic tractography Sherbondy, A. J., Dougherty, R. F., Napel, S. and Wandell, B. A. *Identifying the human optic radiation using diffusion imaging and fiber tractography. Journal of vision,* 8(10), pp. 12-12 (2008. For this purpose two sROIs are needed to define the extremities of the tract. Manual delineation of the LGN ground-truth is performed on the PDD map. It is approximated by a 7 mm-radius sphere indicated by white circles 302 of PPD map 304 as described with reference to FIG. 3. The sphere usually contains reddish voxels as most optic radiation fibers leave the LGN medially.

Figure 9:
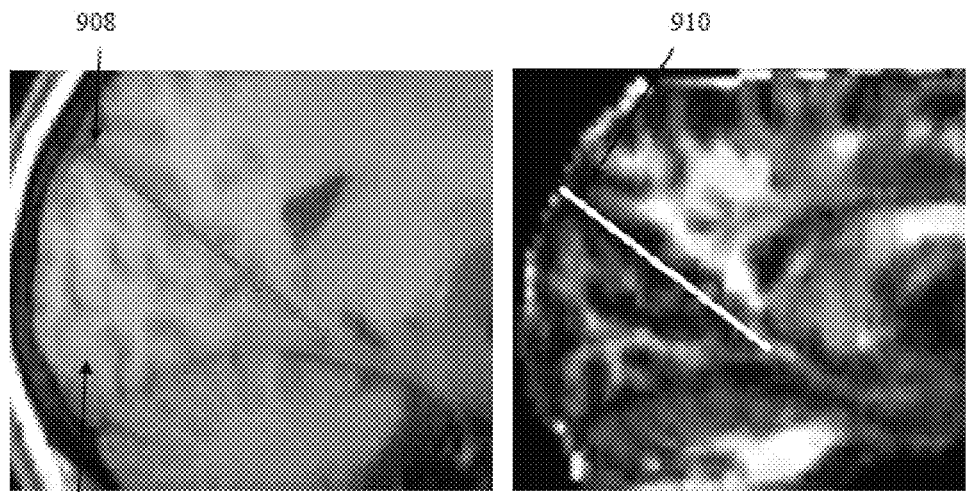
FIG. 9 includes imagers which depict ground truth definitions of the calcarine sulcus sROI on a sagittal view for the computational evaluation, in accordance with some embodiments of the present invention.

Reference is now made to FIG. 9, which includes images depicting ground truth definitions of the calcarine sulcus sROI on a sagittal view for the computational evaluation, in accordance with some embodiments of the present invention. Reference to the calcarine sulcus is delineated as a complex 3-D volume 902 on high resolution T1w images 904. The PDD image 906 does not provide sufficient spatial resolution for the manual delineation of the calcarine. Lines 908 and 910 delimit the occipital and parietal lobes.

The Motor Tract

The motor tract connects the precentral-gyrus (posterior frontal lobe) to the brain stem and spinal cord. Probabilistic tractography is a preferred choice also for motor tract reconstruction as it crosses many others on its way to lateral motor areas (e.g. face, mouth, lips). Therefore, two sROIs are needed to define the extremities of the tract.

Figure 10:
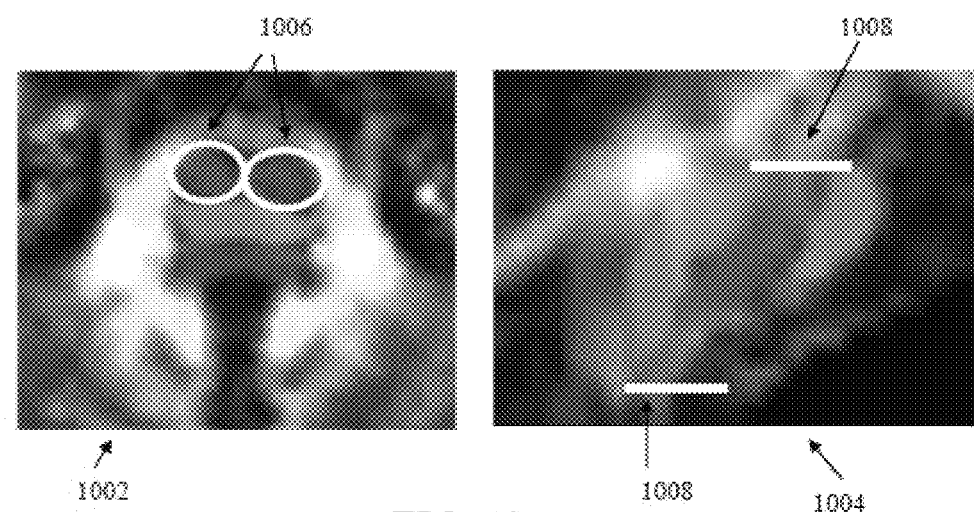
FIG. 10 includes images depicting ground truth definition of the brainstem sROIs for the computational evaluation, in accordance with some embodiments of the present invention.

Reference is now made to FIG. 10, which includes images depicting ground truth definition of the brainstem sROIs for the computational evaluation, in accordance with some embodiments of the present invention. sROI are defined in the brainstem for axial 1002 and sagittal 1004 views in the PDD map. The sROI are denoted by the PDD volume (e.g., appears blueish in color images) delimited axially by the circles 1006 and vertically by the line segments 1008. In the axial view, each circle corresponds to the sROI for a distinct brain hemisphere.

Manual delineation of the precentral gyrus sROI is usually based on a high resolution T1w image 308 as shown in FIG. 3. The hand notch pattern 310 is helpful in detecting the precentral gyms 312, but still the task is tedious and requires neuroanatomic expertise.

The Arcuate Fasciculus

The arcuate fasciculus connects between Wernicke and Broca language areas that are critical to language understanding and generation, respectively. It also provides many other less-known connections resulting in many dispersed extremities. In this situation, probabilistic tractography is impractical as a pair of sROIs that seed the whole tract cannot be defined. Hence, deterministic tractography will be preferred in this case, with one sROI serving for proper fiber seeding and a second one to spatially constrain the seeded fibers through a logical and operation in order to remove outliers. On T1w images, the arcuate is difficult to localize accurately. Therefore, the ground truth for its sROIs is obtained on the PDD map.

Figure 11:
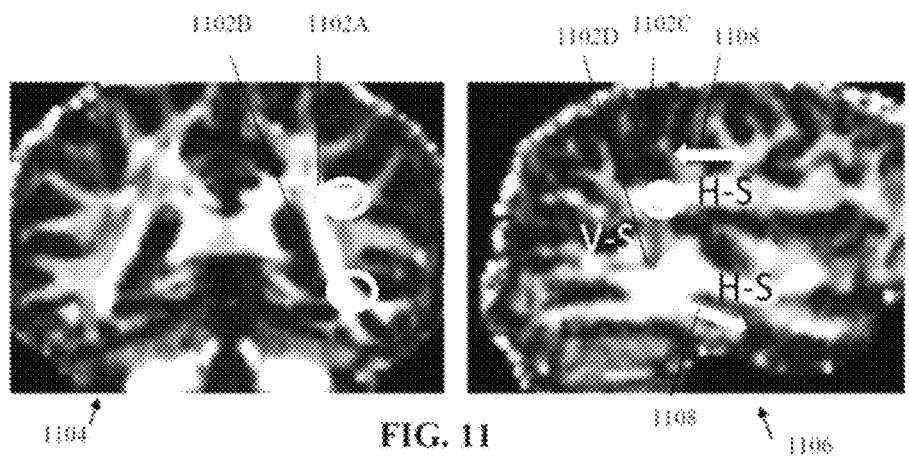
FIG. 11 includes images depicting ground truth definition for the calcarine sulcus sROIs on the PPD maps, for the computational evaluation, in accordance with some embodiments of the present invention.

Reference is now made to FIG. 11, which includes images depicting ground truth definition for the calcarine sulcus sROIs on the PPD maps, for the computational evaluation, in accordance with some embodiments of the present invention. Arcuate sROIs pairs 1102A-D are depicted on coronal 1104 and sagittal 1106 PDD maps. sROIS 1102 are sections of the arcuate approximated by a 7 mm-radius sphere. The upper circle 1102A 1102C indicates the actual seeding while the lower circle 1102B 1102D provides the additional spatial constraint. The location of the upper and lower circles 1102A-D corresponds to the beginning and end, respectively, of the vertical arcuate segment (V-S), where it connects to upper and lower (quasi) horizontal segments (H-S). Note that, in comparison to the other tracts' sROIs, a higher ambiguity exists about the optimal position of the sROIs. In fact, since the arcuate's sROIs are not located at its extremities, shifting them by 10-20 mm (as illustrated by the arrows 1108) along the arcuate would not result in a significantly different tract.

Preprocessing

Rigid registration between B0 and the T1w scan was computed by MrDiffusion for each case in the dataset. Non-brain voxels were removed from the images using a coarse binary mask obtained by thresholding the B0 image intensity, followed by morphological hole closing. Exploiting the previous registration between B0 and T1w, the mask is projected onto both PDD and T1W volumes. Slices that do not contain mask voxels are eliminated.

To tackle memory limitations during the consecutive processing by the 3-D FCNNs, 3-D cropping is further applied to the dataset. For this purpose, the 3-D bounding box (3DBB) of the coarse binary mask is computed for each brain. Note that the 3DBB contains the whole brain. For each tract type, a fixed size cropping box is then defined and positioned.

Figure 12:
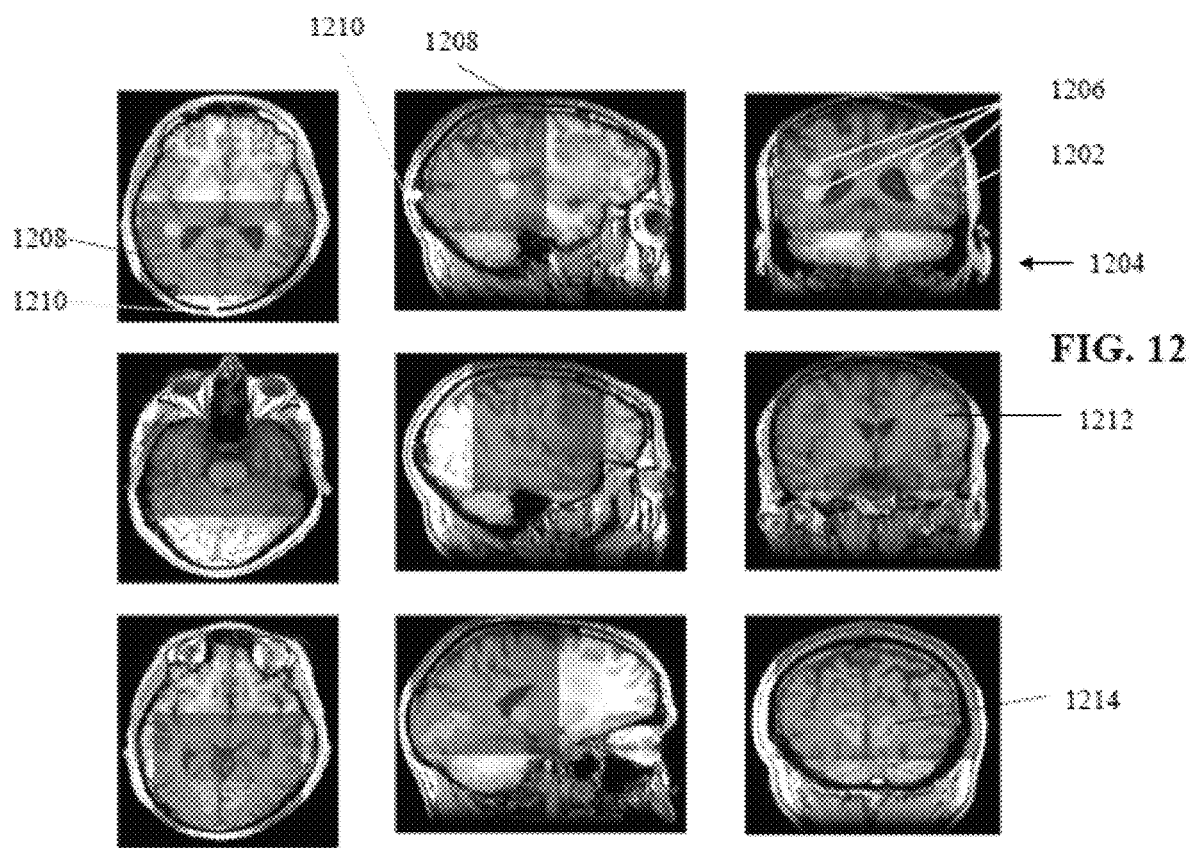
FIG. 12 includes images depicts cuboid cropping boxes in transparent overlay to the brain image and the corresponding sROIs for the arcuate (top row), motor (middle row), and optic radiation (bottom row) tracts, in accordance with some embodiments of the present invention.

Reference is now made to FIG. 12, which includes images depicting cuboid cropping boxes 1202 in transparent overlay to the brain image 1204 and the corresponding sROIs for the arcuate 1206 (top row), motor 1212 (middle row), and optic radiation 1214 (bottom row) tracts, in accordance with some embodiments of the present invention. Axial (left column), sagittal (center column), and coronal (right column) views are presented. One image is marked for each type of sROI for simplicity and clarity of explanation.

Reference is now made to FIG. 13, which includes a Table 1302 summarizing a fixed size cropping box that is defined and positioned for each tract type, for the computational evaluation, in accordance with some embodiments of the present invention. The third column in Table 1302 gives the offset vector between the upper-left-posterior corner (ULPC) of the 3DBB and the ULPC for the considered sROIs cropping box. For example, the Arcuate blue cropping box 1208 of FIG. 12 has been shifted forward by 10 mm (as denoted by arrows 1210).

Implementations

The performance of the proposed exemplary W-net and Y-net multi-modality classifier architectures based on the statistical classifier described herein are compared to the V-net described with reference to Milletari. For comparison to Wnet and Ynet, the Vnet was also implemented for three different input types: T1w, PDD, and PDD-T1w. The first two implementations are of single modalities, while in the last one, T1w is stacked as an additional, $4^{th}$ channel, upon the 3 PDD channels.

All the architectures were implemented using the Tensor-Flow framework (e.g., available at www(dot)tensorflow (dot)org/). The architectures were compared over 5 cross-validation folds for each tract sROIs. The fold consisted of 60 training cases and 15 test cases. Each classifier architecture was trained to segment the left and right sROIs for the corresponding tract, resulting in four different labels for the sROIs and one for the background (rest of the brain). The test cases were chosen randomly, without overlap. As proposed in He, K., Zhang, X., Ren, S. and Sun, J. *Delving deep into rectifiers: Surpassing human-level performance on Imagenet classification. In Proceedings of the IEEE international conference on computer vision*, pp. 1026-1034 (2015) and used in Kamnitsas, K., Ledig, C., Newcombe, V. F., Simpson, J. P., Kane, A. D., Menon, D. K., Rueckert, D., and Glocker, B. *Efficient multi-scale 3D CNN with fully connected CRF for accurate brain lesion segmentation. arXiv:* 1603.05959 (2016) and Dolz J, Desrosiers C, Ayed I B. 3*D* fully convolutional networks for subcortical segmentation in MRI: A large-scale study. arXiv:1612.03925, 2016, all the network parameters (i.e., kernel weights) were initialized using a zero-mean Gaussian distribution with standard deviation of $\sqrt{2/n^l}$, where $n^l$ denotes the number of connections to the units in layer l. For example, if the input is composed of three channels and the kernel size is 5×5×5, the standard deviation is equal to $\sqrt{2/(3\times5\times5\times5)}$=0.073. The PRelu parameters were initialed to zeros. The initialization leads to a better convergence than the assignment of normally-distributed random values to the kernel and bias weights. The dropout keep probability was set to 0.5.

Training was performed by an Adam optimizer, described with reference to Kingma, D. and Ba, J.: Adam: *A method for stochastic optimization. arXiv*:1412.6980 (2014) (hereinafter "Kingma"), with an initial learning rate of 0.0001 and a batch size of a single (brain) volume. Each multi-modal classifier architecture was trained end to end, from scratch, for 100 epochs or until convergence, whichever came first. Mean Dice greater than 0.9 was defined as convergence. Both training and testing were performed on a windows workstation equipped with 32 GB of memory, an Intel® Core™ i7-4790 CPU working at 3.60 GHz, and an NVidia GTX 1070 GPU with 8 GB of video memory.

Results

Figure 14:
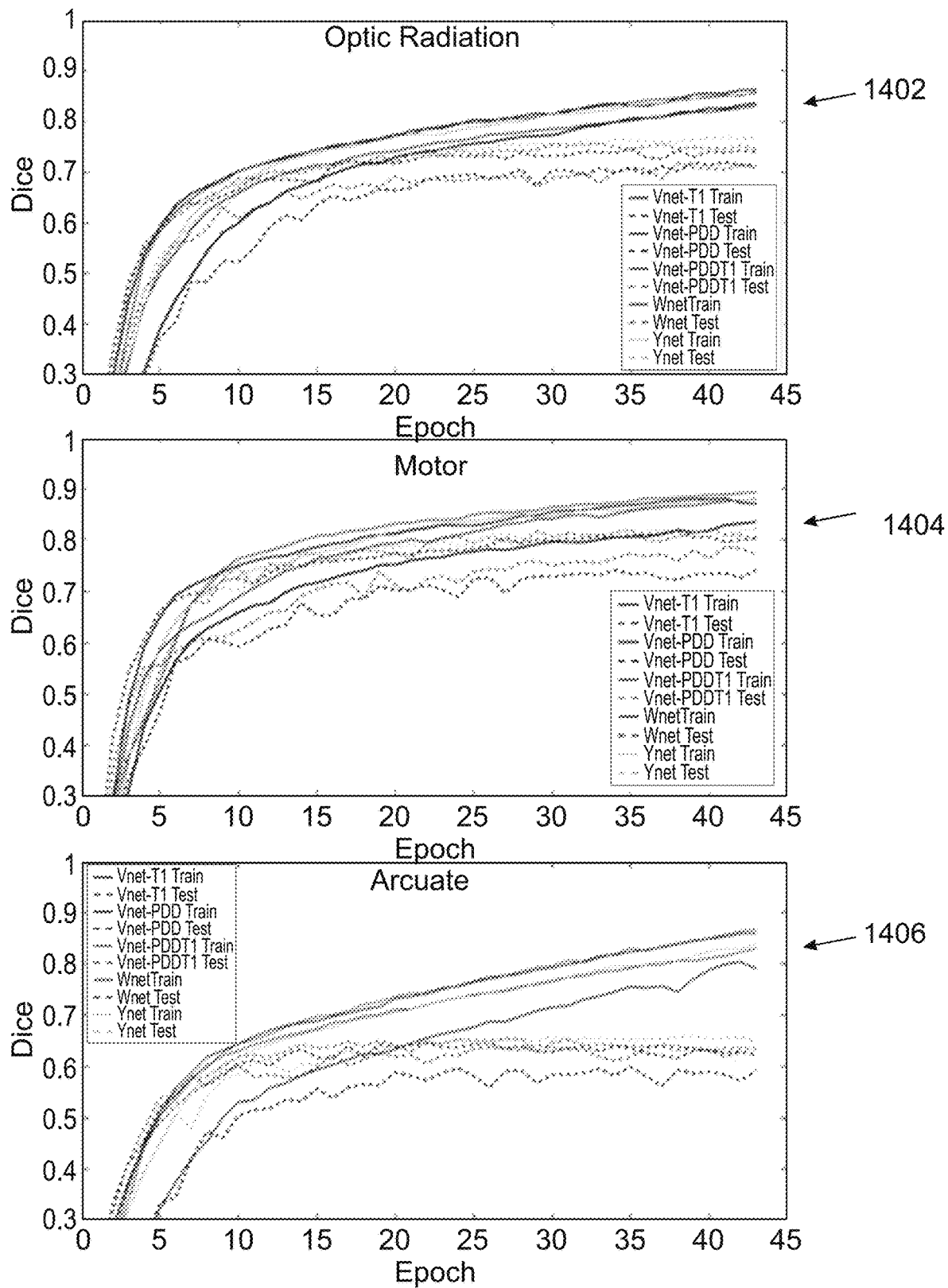
FIG. 14 includes graphs depicting mean Dice values obtained for the compared classifiers, for the training and testing stages, as a function of number of training Epochs for Optic radiation, Motor, and Arcuate sROIs of the computational evaluation, in accordance with some embodiments of the present invention.

Reference is now made to FIG. 14, which includes graphs depicting mean Dice values obtained for the compared classifiers, for the training and testing stages, as a function of number of training Epochs for Optic radiation 1402, Motor, 1404, and Arcuate 1406 sROIs of the computational evaluation, in accordance with some embodiments of the present invention. It is noted that the testing mean DICE values at a given epoch are obtained by forwarding the test cases through the network to compute loss only, without back-propagation, as these cases are by definition not part of the training set. Vnet is evaluated for PDD (denoted Vnet-PDD), T1w (Vnet-T1), and their composition (Vnet-PDDT1). Wnet and Ynet, being multi-modal by essence, are only considered on PDD+T1w data.

The Mean Dice in graphs 1402-6 is averaged over the 5 cross-validation folds and the 4 SROIs corresponding to the same tract (for example left & right calcarine and LGN for the optic radiation tract). In the graphs 1402-6, continuous lines are for training while dashed lines are for testing. Overall, Ynet seemed to perform better than the other architectures. The largest improvement is observed with regard to Vnet trained on T1w only, suggesting that PDD information provides an important contribution for all the considered sROIs. This also suggests that the multi-model classifier architectures described herein take advantage of data multi-modality.

Figure 15:
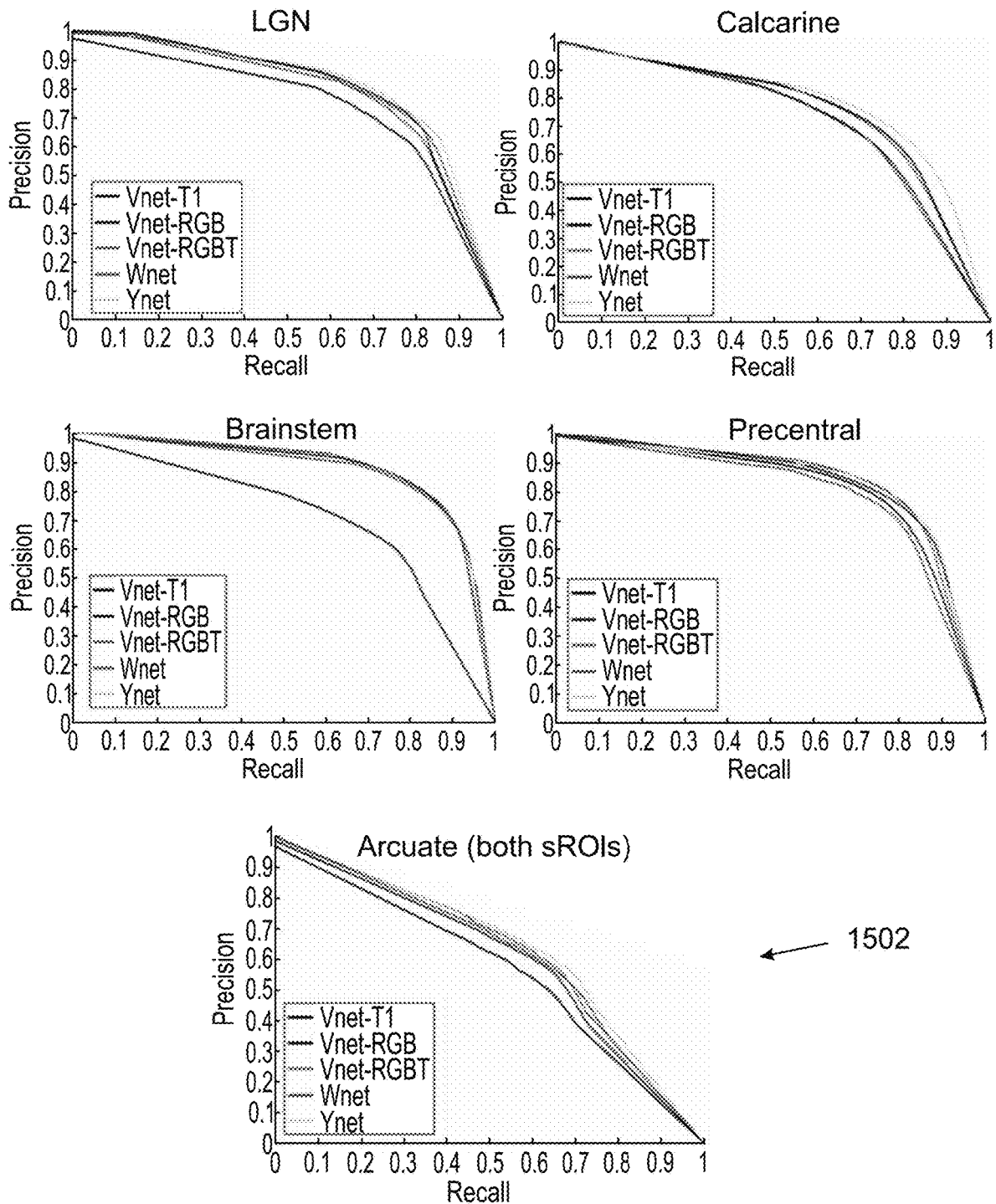
FIG. 15 includes mean precision-recall curves for the 5 folds experiment of the computational evaluation, in accordance with some embodiments of the present invention.

Reference is now made to FIG. 15, which includes mean precision-recall curves for the 5 folds experiment of the computational evaluation, in accordance with some embodiments of the present invention. For the motor and visual sROIs, each curve is an average over the left and right hemisphere segmentations as well as over the 5 cross-validation folds. For the arcuate, further averaging is performed over the sROIs pairs (upper and lower), resulting in a single set of curves for both sROIs, denoted "Arcuate" 1502. Ynet (green) achieved the best results for all the sROIs. This is further confirmed by the area under the curve (AUC) of the precision-recall curves.

Reference is now made to FIG. 16, which is a table 1602 summarizing AUC for the evaluated classifiers (i.e., based on standard practice V-net and the multi-modal classifier architectures described herein, including Y-net and W-net) of the computational evaluation, in accordance with some embodiments of the present invention. As shown (bolded), the Y-net architecture yielded the highest AUC for the 5 cross-validation folds experiment.

Reference is now made to FIG. 17, which is a table 1702 summarizing mean (standard deviation) of the Dice coefficient for sROIs segmentation over the 5 cross-validation folds of the computational evaluation, in accordance with some embodiments of the present invention. A threshold of 0.5 was applied to the softmax score. The Dice coefficient was computed as described with reference to Dice, L. R.: *Measures of the amount of ecologic association between species. Ecology,* 26(3) 297-302 (1945).

Reference is now made to FIG. 18, which is a table 1802 summarizing mean (standard deviation) of the Jaccard coefficient for SROIs segmentation over all the 5 cross-validation folds of the computational evaluation, in accordance with some embodiments of the present invention. A threshold of 0.5 was applied to the softmax score. The Jaccard coefficient was computed as described with reference to Hamers, L. *Similarity measures in scientometric research: The Jaccard index versus Salton's cosine formula. Information Processing and Management,* 25(3), pp. 315-18 (1989).

As shows in table 1802 of FIG. 18 and table 1702 of FIG. 17, the y-net architecture outperformed most of the compared algorithms, only slightly surpassed by Vnet-PDD and Vnet-PDDT1 for the brainstem sROIs.

Considering that automatic tractography is the ultimate purpose of sROI segmentation, the proposed multi-modal classifier architectures (i.e., Y-net and W-net) are further assessed based on the quality of the tractography seeded at the automatic sROIs. For this purpose, tracts are generated between the corresponding pairs of automatic sROIs and the DICE overlap is computed with respect to those seeded at the manually delineated sROIs.

Reference is now made to FIG. 19, which includes a table 1902 presenting main parameter values for probabilistic tractography of the optic radiation and motor tracts of the computational evaluation, in accordance with some embodiments of the present invention.

Reference is also made to FIG. 20, which includes a table 2002 presenting main parameter values for the deterministic tractography of the Arcuate tracts of the computational evaluation, in accordance with some embodiments of the present invention.

The probabilistic tractography algorithm ConTrack, described with reference to Sherbondy, A. J., Dougherty, R. F., Ben-Shachar, M., Napel, S. and Wandell, B. A. *ConTrack: finding the most likely pathways between brain regions using diffusion tractography. Journal of vision,* 8(9), pp. 15-15 (2008) (hereinafter "Sherbondy"), was used to generate the motor and visual fibers. The choice of probabilistic tractography for motor and visual tracts is dictated by the fact both have clearly definable end-points but encounter many fiber crossings on their way. Seeding is started at both sROIs. At each step, the local fiber direction is drawn at random from a probability density function having a mode coinciding with the local tensor PDD, as described by Sherbondy. The main parameter values implemented for the probabilistic tractography are presented in Table 1902 of FIG. 19, the remaining are set as described with reference to www(dot)web(dot)stanford(dot)edu/group/vista/cgi-bin/wiki/index(dot)php/ConTrack. Once the desired number of fibers has been reconstructed between the corresponding sROIs pair, the fibers are sorted according to a quality score reflecting smoothness and fidelity to the local PDD orientation. Only the K-best scoring fibers (as presented in Table 1902 of FIG. 19) are kept in the end, as described with reference to Sherbondy. For the language fibers (Arcuate), a deterministic tractography algorithm is chosen, as end points of the tracts are more difficult to define, making the "exploratory" capability of deterministic tractography a useful feature. The algorithm is based on a fourth order Runge-Kutta integration, with the main parameter values given in Table 2002 of FIG. 20, and as described with reference to www(dot)web(dot)stanford(dot)edu/group/vista/cgi-bin/wiki/index(dot)php/MrDiffusion.

Reference is now made to FIG. 21, which includes is a table 2102 presenting mean (and standard deviation) of the Dice overlap coefficient of the fiber tracts computing by tractography for the computational evaluation, in accordance with some embodiments of the present invention. The best results for the optic radiation and arcuate tracts are obtained for the Ynet architecture. Although the results indicate that Vnet-PDD was better for the motor tract, which is the only case wherein Ynet was outperformed by Vnet-PDD, the visual overlap between manual (blue) and automatic seeding (purple) appears fairly good with Ynet as shown in FIG. 22C.

Reference is now made to FIGS. 22A-D, which are images depicting qualitative results for the Y-net architecture for the optic radiation (FIGS. 22A-B), motor (FIG. 22C), and arcuate (FIG. 22D) sROIs and fiber tracts, in accordance with some embodiments of the present invention.

Figure 22A:
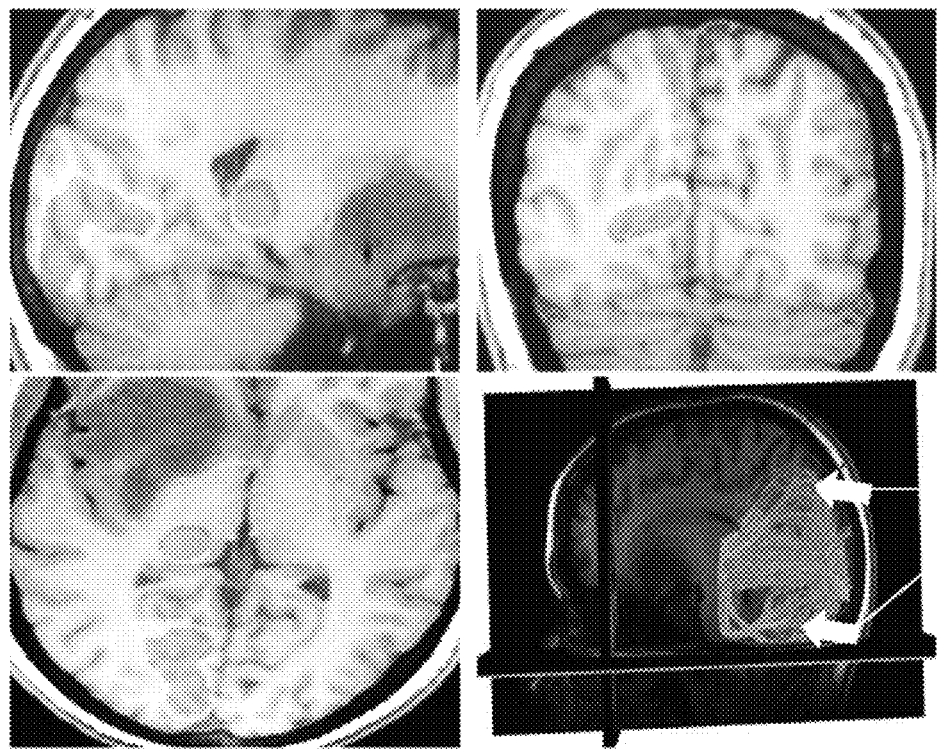
FIGS. 22A-D are images depicting qualitative results for the Y-net architecture for the optic radiation (FIGS. 22A-B), motor (FIG. 22C), and arcuate (FIG. 22D) sROIs and fiber tracts, in accordance with some embodiments of the present invention.
Figure 22B:
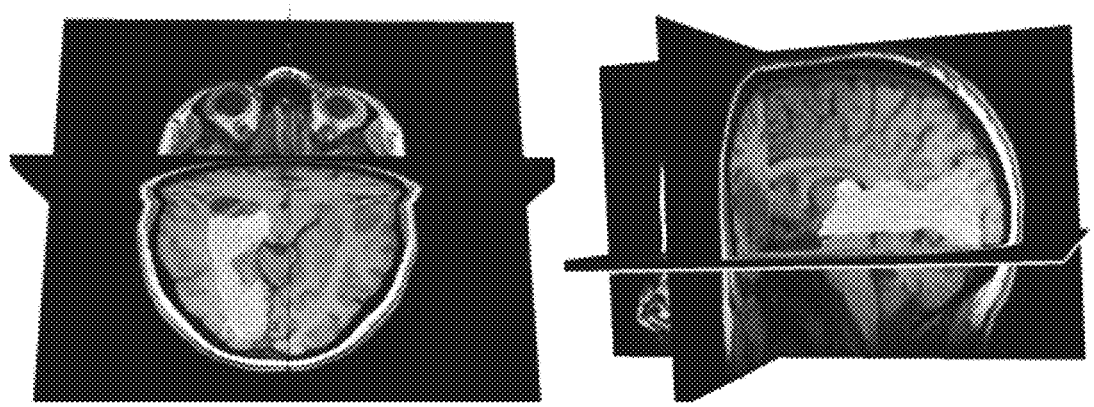
Figure 22C:
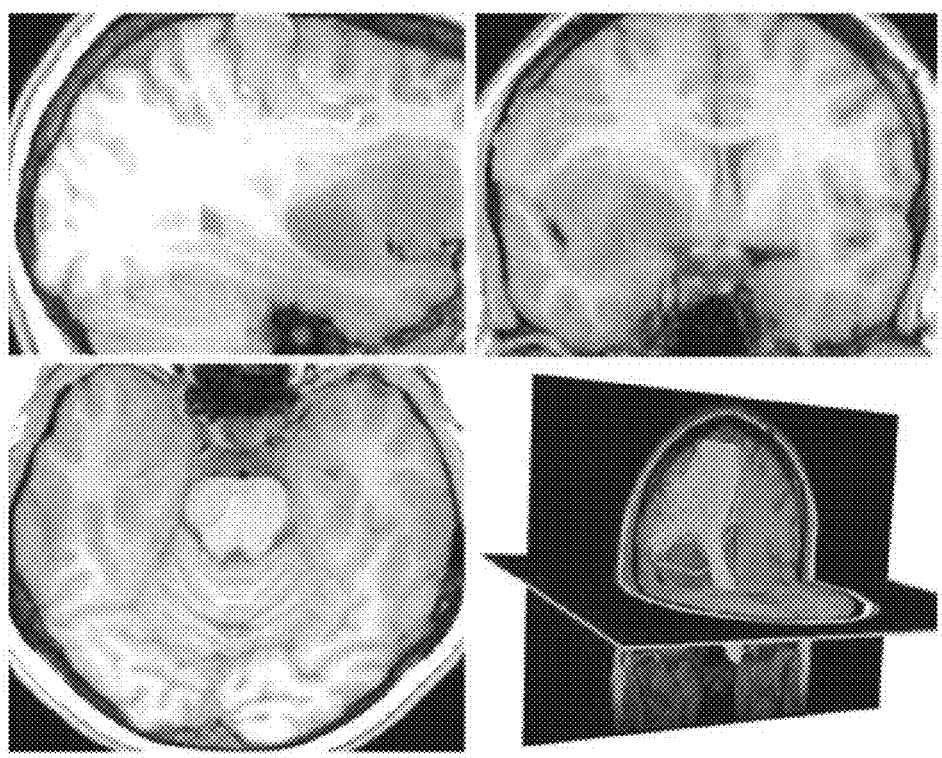
Figure 22D:
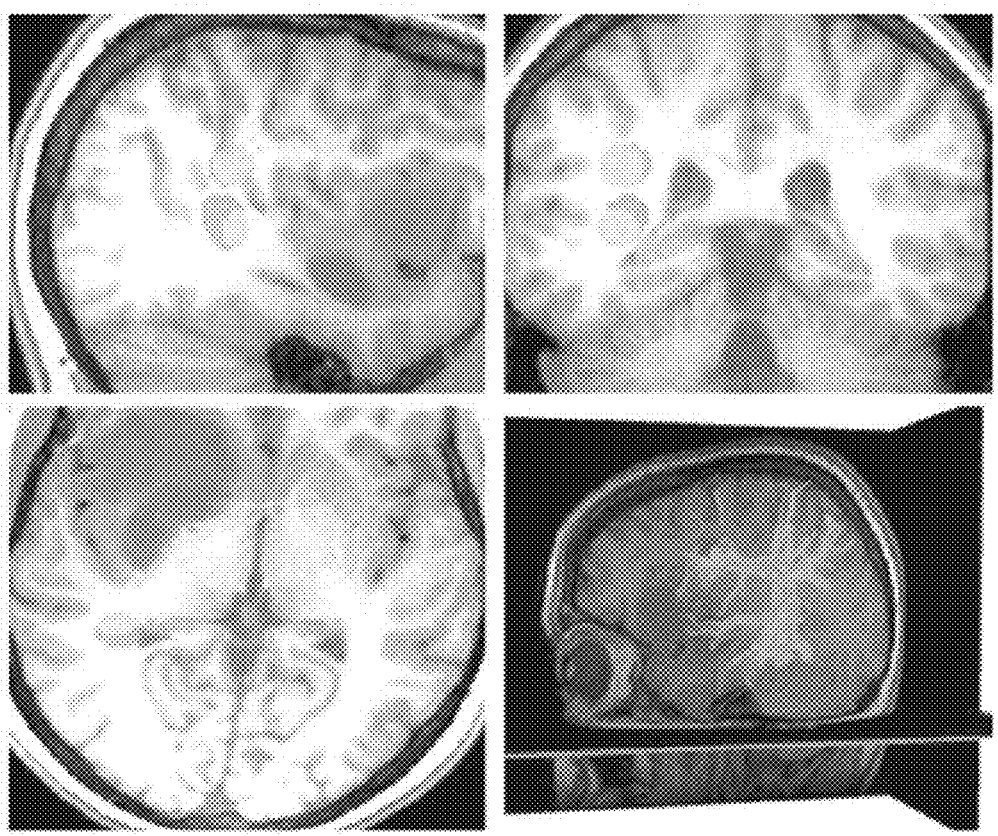

The automatic sROIs (shown as light green in colored images) and the ground truth (shown as red in colored images) are shown in overlay to sample sagittal (top-L), coronal (top-R) and axial (bottom-L) T1w sample slices in FIGS. 22A, 22C, and 22D. At perfect overlay, the sROI color becomes a dark green in colored images. The resulting tracts (bottom-R, FIGS. 22A, 22C, and 22D) are shown for both automatic (purple fibers in colored images) and manual (blue fibers in colored images) seeding. For the optic radiation and motor tracts (FIGS. 22A, and 22C), a good overlap is observed between automatic and manual sROIs as confirmed by the DICE and Jaccard scores of Tables 1702 of FIG. 17 and Table 1802 of FIG. 18, respectively.

At first glance, the results for arcuate's sROIs may appear less than satisfactory, reflecting a smaller overlap (FIG. 22D) as confirmed in Tables 1702 of FIG. 17 and Table 1802 of FIG. 18. Nevertheless, the resulting arcuate fiber tracts (FIG. 22D, bottom-R) exhibit an overlap between the automatic (shown in purple in colored images) and manual (shown in blue in colored images) seeding which is fairly similar to the overlap in the other tracts, as verified in Table 2102 of FIG. 21. This effect may be explained by the higher acceptable ambiguity on the position of the arcuate sROIs, as described herein. Even though the arcuate sROIs appear a bit shifted, they are still crossed by the expected tract segment. Automatically-seeded and manually-seeded fiber tracts for the optic radiation (FIG. 22A, bottom-R) also show a good overlap. Note that many fiber outliers appear in the optic radiation tractography (arrows 2202). These are caused by the tractography algorithm and are present both in automatically (shown in purple in colored images) and manually (shown in blue in colored images) seeded fibers. Outliers are easily removed by manual editing, resulting in the very clean tracts of FIG. 22B in which the excellent overlap between automatic (shown in purple in colored images) and manual (shown in blue in colored images) tracts is clearly visible.

CONCLUSION

As described herein, Inventors performed a computational evaluation of two implementations of the multi-modal classifier (e.g., based on FCNN architectures) for automatic segmentation of tractography seeding ROIs. The implementations of the architectures that were evaluated are differentiated by the stage at which modality fusion occurs and its span along the network: While in Wnet the modalities are fused in a single concatenation step, right before final segmentation, in Ynet, the fusion spans the whole synthesis path, as described herein. In most of the experiments, the Ynet architecture has outperformed Wnet as well as single-modality Vnet and its straightforward multi-modality extension in which the different modalities are already fused (appended) at the network input. The results suggest that the Ynet approach to modality fusion is advantageous for the task. The proposed classifier(s) may better exploit multi-modal information than the human expert which will usually exclusively rely on PDD or T1w, depending on the sROI that has to be manually segmented.

The processing time of a new case by the trained networks is only of a few seconds (1-2 sec). Adding memory to the GPU card should eliminate the need for the cuboid cropping box that was used to cope with memory limitations.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images and DTI images will be developed and the scope of the terms anatomical images and DTI images are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method of automatic segmentation of at least one three dimensional (3D) anatomical region of interest (ROI) that delineates at least one predefined anatomical structure of a target individual, comprising:

receiving a plurality of 3D images of a target individual, each 3D image of the plurality of 3D images including the at least one predefined anatomical structure, each 3D image of the plurality of 3D images is based on a different respective imaging modality;

inputting each respective 3D image of the plurality of 3D images into a respective processing component of a plurality of processing components of a multi-modal neural network, wherein each processing component of the multi-modal neural network independently computes a respective intermediate output of a plurality of intermediate outputs for the corresponding respective 3D image of the plurality of 3D images, wherein each respective processing component of the plurality of processing components comprises 3D convolutional filters, and the intermediate outputs comprises a plurality of features obtained as outcomes of the 3D convolutional filters;

inputting the plurality of intermediate outputs comprising the plurality of features obtained as outcomes of the 3D convolutional filters into a common at least one last convolutional layer comprising 3D convolutional filters; and computing an indication of a segmented at least one 3D ROI that delineates the at least one predefined anatomical structure, for each of the plurality of 3D images, by the common at least one last convolutional layer comprising 3D convolutional filters.

2. The method according to claim 1, wherein each of the plurality of processing components includes an encoding-contracting path for capturing context based on a plurality of computed feature channels, and a decoding-expanding path for localization based on the computed features.

3. The method according to claim 1, wherein the at least one last convolutional layer comprises a fully connected layer.

4. The method according to claim 1, wherein features extracted from stages of the encoding-decoding path are forwarded to corresponding stages of the decoding-expanding path for gathering fine grained detail that would otherwise be lost in compression computations of the encoding-contracting path.

5. The method according to claim 1, wherein the plurality of 3D images are registered to one another, and wherein the indication of the segmentation of the at least one 3D ROI is associated with each of the plurality of registered 3D image.

6. The method according to claim 1, wherein the plurality of 3D images include a 3D MRI anatomical image of a brain of a target individual, and a 3D diffusion tensor imaging (DTI) image of the brain indicative of principal direction of diffusion (PDD), and the at least one 3D ROI includes at least one predefined brain structure.

7. The method of claim 6, wherein the 3D anatomical image comprises a T1w magnetic resonance imaging (MRI) image of the brain containing data insufficient for imaging of at least one white matter tract, and the 3D DTI image indicative of PDD comprises a color map.

8. The method according to claim 1, wherein the plurality of 3D images include a T2 weighted MRI scan that includes a prostate, a diffusion weighted MRI that includes the prostate, and a dynamic contrast enhanced scan of the prostate, wherein the at least one 3D ROI includes the prostate.

9. The method according to claim 1, wherein each processing component of the plurality of processing components includes concatenation skips between parallel stages, residual skips in each stage, convolutions and deconvolutions for down and up-sampling, followed by dropout layers.

10. The method according to claim 1, further comprising generating instructions according to the segmented at least one 3D ROI for execution by at least one hardware processor.

11. The method according to claim 10, wherein the instructions are selected from the group consisting of: automatically computing tractography using the at least one 3D ROI, automated surgery by a surgical robot for operating on the at least one 3D ROI, surgical planning for surgery on the at least one 3D ROI, and surgical assistance during surgery on the at least one 3D ROI.

12. The method according to claim 1, wherein the segmented at least one 3D ROI are selected from the group consisting of: lateral geniculate nucleus (LGN) of the thalamus, calcarine sulcus in the occipital lobe, precentral-gyrus (posterior frontal lobe), brain stem, Wernicke area, and Broca area, motor tract, sensory tract, arcuate fasciculus, optic radiation tract, and prostate tissues including tumors and lesions.

13. The method according to claim 12, further comprising automatically computing brain tracts by at least one processor that executes code for automated tractography using the at least one 3D ROI as a seed ROI, selected from the group consisting of: computing an optic radiation tract using the LGN and calcarine sulcus segmented ROIs as seed ROIs, computing a motor tract using the precentral-gyrus and brain stem segmented ROIs as seed ROIs, and computing an arcuate tract using the Wernicke and Broca segmented ROIs as seed ROIs.

14. A computer implemented method of automatic segmentation of at least one three dimensional (3D) anatomical region of interest (ROI) that delineates at least one predefined anatomical structure of a target individual, comprising:
  receiving a plurality of 3D images of a target individual, each 3D image of the plurality of 3D images including the at least one predefined anatomical structure, each 3D image of the plurality of 3D images is based on a different respective imaging modality;
  inputting each respective 3D image of the plurality of 3D images into a respective encoding-contracting component of a plurality of encoding-contracting components of a multi-modal neural network, wherein each encoding-contracting component of the multi-modal neural network independently computes a respective intermediate output of a plurality of intermediate outputs for the corresponding respective 3D image of the plurality of 3D images,
  wherein each respective processing component of the plurality of processing components comprises 3D convolutional filters, and the intermediate outputs comprises a plurality of features obtained as outcomes of the 3D convolutional filters;
  inputting the plurality of intermediate outputs comprising the plurality of features obtained as outcomes of the 3D convolutional filters into a single common decoding-expanding component of the multi-modal neural network comprising 3D convolutional filters; and
  computing an indication of a segmented at least one 3D ROI that delineates the at least one predefined anatomical structure for each of the plurality of 3D images by the single common decoding-expanding component comprising 3D convolutional filters,
  wherein each stage of the single common decoding-expansion path is concatenated by skips of a plurality of outputs generated by each corresponding stage of each of the plurality of encoding-contracting components and comprises 3D convolutional filters.

15. A computer implemented method of training a multi-modal neural network for outputting an automatic segmentation of at least one three dimensional (3D) anatomical region of interest (ROI) that delineates at least one predefined anatomical structure of a target individual, comprising:
  receiving a plurality of training sets each of a respective sample individual, each training set including a plurality of registered 3D images created based on different imaging modalities and depicting at least one predefined anatomical structure;
  receiving, for each of the plurality of training sets, a 3D segmentation of at least one anatomical ROI that delineates the at least one predefined anatomical structure for each of the plurality of registered 3D images of the respective training sets; and
  training a multi-modal neural network to compute the at least one anatomical ROI that delineates the at least one predefined anatomical structure according to an input of a set of a plurality of registered 3D images based on the different imaging modalities,
  wherein each processing component of the multi-modal neural network independently computes a respective intermediate output of a plurality of intermediate outputs for the corresponding respective 3D image of the plurality of 3D images,
  wherein each respective processing component of the plurality of processing components comprises 3D convolutional filters, and the intermediate outputs comprises a plurality of features obtained as outcomes of the 3D convolutional filters,
  wherein the plurality of intermediate outputs of the plurality of processing components comprising the plurality of features obtained as outcomes of the 3D convolutional filters are merged before at least one last convolutional layer of the multi-modal neural network and the merged plurality of intermediate outputs are inputted into the at least one last convolutional layer comprising 3D convolutional filters.

16. The computer implemented method of claim 15, wherein the multi-modal neural network is trained according to maximization of an objective function based on the registered 3D images indicative of an imbalance between the number of voxels associated with a plurality of 3D anatomical ROIs segmented in parallel and background denoted by the voxels associated with the remaining tissue external to the anatomical ROIs.

17. The computer implemented method of claim 15, wherein the objective function denoted as MeanDice is computed according to the relationship:

$$MeanDice = \frac{1}{L}\sum_{l=1}^{L} D_l$$

wherein:

$$D_l = \frac{2\sum_{i}^{N} p_{li} g_{li}}{\sum_{i}^{N} p_{li}^2 + \sum_{i}^{N} g_{li}^2};$$

$p_{li} \in [0,1]$ denotes a softmax score computed for label l in voxel i,
  $g_{li}$ denotes a binary value indicative of ground truth label l in voxel i.

18. The computer implemented method of claim 15, further comprising cropping each of the plurality of registered 3D images to predefined voxel dimensions defined by a cuboid bounding box including the 3D segmentation of at least one anatomical ROI.

19. The computer implemented method of claim 18, wherein the cuboid bounding box is computed according to a reference cuboid bounding box automatically extracted from a reference image of the respective sample individual that includes the at least one predefined anatomical structure.

* * * * *